US009387182B2

(12) United States Patent
Kikuchi et al.

(10) Patent No.: US 9,387,182 B2
(45) Date of Patent: *Jul. 12, 2016

(54) CARBOSTYRIL DERIVATIVES AND SEROTONIN REUPTAKE INHIBITORS FOR TREATMENT OF MOOD DISORDERS

(71) Applicant: OTSUKA PHARMACEUTICAL CO., LTD., Tokyo (JP)

(72) Inventors: Tetsuro Kikuchi, Tokushima (JP); Taro Iwamoto, Princeton, NJ (US); Tsuyoshi Hirose, Tokushima (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/252,907

(22) Filed: Apr. 15, 2014

(65) Prior Publication Data

US 2014/0221388 A1 Aug. 7, 2014

Related U.S. Application Data

(62) Division of application No. 10/540,577, filed as application No. PCT/JP03/16724 on Dec. 25, 2003, now Pat. No. 8,759,350.

(60) Provisional application No. 60/470,481, filed on May 14, 2003.

(30) Foreign Application Priority Data

Dec. 27, 2002 (JP) ................................. 2002-379003

(51) Int. Cl.
*A61K 31/496* (2006.01)
*A61K 31/501* (2006.01)
(Continued)

(52) U.S. Cl.
CPC ............. *A61K 31/137* (2013.01); *A61K 31/135* (2013.01); *A61K 31/138* (2013.01);
(Continued)

(58) Field of Classification Search
CPC . A61K 2300/00; A61K 31/135; A61K 31/15; A61K 31/165; A61K 31/343; A61K 31/381; A61K 31/4525; A61K 31/496; A61K 31/137; A61K 31/138
See application file for complete search history.

(56) References Cited

U.S. PATENT DOCUMENTS

| 4,310,524 A | 1/1982 | Wiech et al. |
| 5,006,528 A | 4/1991 | Oshiro et al. |

(Continued)

FOREIGN PATENT DOCUMENTS

| CA | 2529857 A1 | 2/2004 |
| CA | 2503121 A1 | 5/2004 |

(Continued)

OTHER PUBLICATIONS

Winans (American Journal of Health-system and pharmacy, vol. 60, Dec. 1, 2003; p. 2437-2447.*

(Continued)

*Primary Examiner* — Savitha Rao
(74) *Attorney, Agent, or Firm* — Finnegan, Henderson, Farabow, Garrett & Dunner, LLP

(57) ABSTRACT

The pharmaceutical composition of the present invention comprises (1) a carbostyril derivative and (2) a serotonin reuptake inhibitor in a pharmaceutically acceptable carrier. The carbostyril derivative may be aripiprazole or a metabolite thereof, which is a dopamine-serotonin system stabilizer. The serotonin reuptake inhibitor may be fluoxetine, duloxetine, venlafaxine, milnacipran, citalopram, fluvoxamine, paroxetine, sertraline or escitalopram. The pharmaceutical composition of the present invention is useful for treating patients with mood disorders, particularly depression or major depressive disorder.

32 Claims, 8 Drawing Sheets

(51) Int. Cl.
*A61K 31/34* (2006.01)
*A61K 31/137* (2006.01)
*A61K 31/135* (2006.01)
*A61K 31/15* (2006.01)
*A61K 31/165* (2006.01)
*A61K 31/343* (2006.01)
*A61K 31/381* (2006.01)
*A61K 31/4525* (2006.01)
*A61K 31/138* (2006.01)

(52) U.S. Cl.
CPC .............. *A61K 31/15* (2013.01); *A61K 31/165* (2013.01); *A61K 31/343* (2013.01); *A61K 31/381* (2013.01); *A61K 31/4525* (2013.01); *A61K 31/496* (2013.01)

(56) References Cited

U.S. PATENT DOCUMENTS

| | | | |
|---|---|---|---|
| 5,500,343 | A | 3/1996 | Blum et al. |
| 5,589,512 | A | 12/1996 | Norden |
| 5,591,884 | A | 1/1997 | DeNinno et al. |
| 5,663,167 | A | 9/1997 | Pickar et al. |
| 5,780,051 | A | 7/1998 | Eswara et al. |
| 5,945,416 | A | 8/1999 | Shannon et al. |
| 5,958,921 | A | 9/1999 | Tollefson |
| 6,066,643 | A | 5/2000 | Perry |
| 6,121,259 | A | 9/2000 | Yelle |
| 6,147,072 | A | 11/2000 | Bymaster et al. |
| 6,150,353 | A | 11/2000 | Broekkamp et al. |
| 6,159,963 | A | 12/2000 | Beasley et al. |
| 6,174,882 | B1 | 1/2001 | Yelle |
| 6,191,133 | B1 | 2/2001 | Coppen |
| 6,322,503 | B1 | 11/2001 | Sparhawk, Jr. |
| 6,348,455 | B1 | 2/2002 | Yelle |
| 6,352,984 | B1 | 3/2002 | Yetle |
| 6,395,727 | B1 | 5/2002 | Guadagno et al. |
| 6,399,608 | B1 | 6/2002 | Dawson |
| 6,582,737 | B2 | 6/2003 | Hirsh et al. |
| 6,960,577 | B2 | 11/2005 | Tollefson |
| 2001/0048943 | A1 | 12/2001 | Faour et al. |
| 2002/0016325 | A1 | 2/2002 | Taylor |
| 2002/0035145 | A1 | 3/2002 | Tsai et al. |
| 2002/0040041 | A1 | 4/2002 | Taylor |
| 2002/0051807 | A1 | 5/2002 | Faour et al. |
| 2002/0123490 | A1 | 9/2002 | Howard |
| 2002/0156067 | A1 | 10/2002 | Wong et al. |
| 2002/0173513 | A1 | 11/2002 | Jordan et al. |
| 2003/0027817 | A1 | 2/2003 | Tollefson |
| 2003/0049308 | A1 | 3/2003 | Theobald |
| 2003/0109546 | A1 | 6/2003 | Fenton |
| 2003/0130334 | A1 | 7/2003 | Muller |
| 2004/0058935 | A1 | 3/2004 | Bando et al. |
| 2004/0204401 | A1 | 10/2004 | Migaly |
| 2005/0038015 | A1 | 2/2005 | Bronzova et al. |
| 2006/0287299 | A1 | 12/2006 | Sheldon |

FOREIGN PATENT DOCUMENTS

| | | |
|---|---|---|
| CA | 2503201 A1 | 5/2004 |
| EP | 0958824 A2 | 11/1999 |
| EP | 0966967 A2 | 12/1999 |
| EP | 1238676 A1 | 9/2002 |
| JP | 2002-515435 | 5/2002 |
| RU | 94037967 A1 | 8/1996 |
| RU | 2181287 C | 4/2002 |
| WO | 95/00154 | 1/1995 |
| WO | 97/35584 A1 | 10/1997 |
| WO | 98/11897 | 3/1998 |
| WO | 99/58130 | 11/1999 |
| WO | 99/59593 | 11/1999 |
| WO | 99/61027 | 12/1999 |
| WO | 99/62522 | 12/1999 |
| WO | 00/59489 A2 | 10/2000 |
| WO | 01/19371 A1 | 3/2001 |
| WO | 01/51040 | 7/2001 |
| WO | 01/51041 | 7/2001 |
| WO | 01/80837 | 11/2001 |
| WO | 02/053140 | 7/2002 |
| WO | 02/060423 | 8/2002 |
| WO | 02/072145 | 9/2002 |
| WO | 02/085839 | 10/2002 |
| WO | 03026659 | 4/2003 |
| WO | 03/066039 A1 | 8/2003 |
| WO | 03/068207 A2 | 8/2003 |
| WO | 03101492 A3 | 12/2003 |
| WO | 2004/010932 A2 | 2/2004 |
| WO | 2004/011031 A1 | 2/2004 |
| WO | 2005023265 A1 | 3/2005 |
| WO | 2005051488 A1 | 6/2005 |
| WO | 2005053703 A1 | 6/2005 |

OTHER PUBLICATIONS

U.S. Appl. No. 60/319,736, Peter Migaly.
U.S. Appl. No. 60/473,378, filed May 23, 2003, Tetsuro Kikuchi et al.
Adli, M. et al. "Algorithms for optimizing the treatment of depression: making the right decision at the right time", Pharmacopsychiatry, Nov. 2003, Supp 3:S222-9.
American Academy of Pediatrics, Committee on Nutrition, The Use and Misuse of Fruit Juice in Pediatrics Pediatrics (2001) vol. 107, No. 5, pp. 1210-1213.
Aoki S. et al., "Study on Crystal Transformation of Aripiprazole", The fourth Japan-Korea Symposium on Separation Technology, 1996.
Armstrong, et al., Blood Clozapine Levels Elevated by Fluvoxamine: Potential for Side Effects and Lower Clozapine Dosage, Journal of Clinical Psychiatry, 1997, vol. 58, No. 11, p. 499.
Azhar, M. Z. Comparison of fluvoxamine alone, fluvoxamine and cognitive psychotherapy and psychotherapy alone in the treatment of panic disorder in Kelantan—implications for management by family doctors. Med J Malaysia 2000 55(4)402-8.
Baldessarini et al., Hospital Use of Antipsychotic Agents in 1989 and 1993: Stable Dosing With Decreased Length of Stay; American Journal of Psychiatry 152:7, Jul. 1995; pp. 1038-1043.
Bandelow et al., Aripiprazole, a "Dopamine-Serotonin System Stabilizer" in the Treatment of Psychosis; XP009098592; ISSN 1433-1055.
Barbee J G et al's article Lamotrigine as an augmentation agent in treatment-resistant depression. J.Clin Psychiatry 63:8 Aug. 2002 p. 737-741.
Barlow DH Anxiety and its disorders (teamed alarms) pp. 220-225, Guilford Press, 1988.
Battaglia 1 et al Structured assessment and depot fluphenazine treatment of multiple suicide attempters in the emergency department. International Clinical Psychophannacology 1999, 14: 361-372.
Beasely CM et al Olanzapine versus placebo and Haloperidol. Acute phase results of the North American double-blind olanzapine trial. Neuropsychophannacology 14: 111-123 1996.
Green, Ben, Focus on aripiprazole, Current Medical Research and Opinions, 2004, vol. 20, No. 2, pp. 207-213.
Berman et al., "Antidepressant Effects of Ketamine in Depressed Patients," Biological Psychiatry (2000) vol. 47, pp. 351-354.
Bernstein, J.G., Induction of obesity by psychotropic drugs, Ann. NY Acad. Sci., 1987, vol. 499, pp. 203-215.
Bernstein, J.G., Psychotropic drug induced weight gain: mechanisms and management, Clinical Neuropharmacology, 1988, vol. 11, suppl. 1, s194-206.
Blum A Patients at risk of developing severe side effects from depot fluphenazine treatment Am J Psychiatry 137:2 1980 254-255.
Bodkin, et al., Combining Serotonin Reuptake Inhibitors and Bupropion in Partial Responders to Antidepressant Monotherapy, Journal of Clinical Psychiatry, 1997, vol. 58, No. 4, pp. 137-145.
Brody A. et al Regional brain metabolic changes in patients with major depression treated with either paroxetine or Interpersonal therapy. Arch Gen Psychiatry 2001; 58:631-640.
Bymaster, Frank P., "Comparative Affinity of Duloxetine and Venlafaxine for Serotonin and Norepinephrine Transporters in vitro

(56) References Cited

OTHER PUBLICATIONS and in vivo, Human Serotonin Receptor Subtypes, and other Neuronal Receptors", Neuropsychopharmacology, 2001, vol. 25, No. 6, p. 871-880.
Canadian Office Communication dated Oct. 16, 2007.
Casey et al., An integrated cognitive model of panic disorder: The role of positive and negative cognitions Clinical Psychology Review (2004) vol. 24 pp. 529-555.
Cassidy, et al., Addition of Fluoxetine to Clozapine, American Journal of Psychiatry, 1992, vol. 149, No. 9, p. 1274.
Centorrino, et al., Serum Levels of Clozapine and Norclozapine in Patients Treated With Selective Serotonin Reuptake Inhibitors, American Journal of Psychiatry, 1996, vol. 153, No. 6, pp. 820-822.
Chemical Abstracts Registry entry No. 129722-12-9 (aripiprazole), entered into STN on Oct. 5, 1990.
Citrome, et al., Pharmacokinetics and safety of aripiprazole and concomitant mood stabilizers, Neuropsychopharmacology, 2002, vol. 5, suppl. 1.
Georgian Search Report dated Jun. 15, 2006.
Courvoisier, Simone, "Pharmacodynamic Basis for the Use of Chlorpromazine in Psychiatry", Journal of Clinical and Experimental Psychopathology, 1956: vol. 17: p. 25-37.
Cremers TI, et al Is the beneficial antidepressant effect of coadministration of pindolol really due to somatodendritic autoreceptor antagonism? Biol Psychiatry Jul. 1, 2001; 50(1):13-21.
Current Patents Nov. 15, 2002 week 0246 at http://scientific.thompson.com/media/cdjournals/gazettenews/202/CPG_News_0246.pfd—enclosed.].
Czyrak, et al., Pharmacological Effects of Zotepine and other Antipsychotics on the Central $5-HT_2$ Receptors, Pharmacopsychiatry, 1993, vol. 26, No. 2, pp. 53-58.
D. Souery et al.; "Treatment resistant depression: methodological-overview and operational criteria"; European Neuropsychopharmacology; 1999; pp. 83-91; 9; Elsevier Science B.V./ECNP; Amsterdam, The Netherlands.
De Adson, M.D. et al.; "An Open Trial of Quetiapine for Anxiety in Patents Receiving an SSRI"; Society of Biological Psychiatry Annual Meeting; May 16-18, 2002: Philadelphia, Pennsylvania.
Delbello Melissa P. et al., A Double-Blind, Randomized, Placebo-Controlled Study of Quetiapine as Adjunctive Treatment for Adoloescent Mania; XP009098620; J. Am Acad. Child Adolescent Psychiatry 41:10, Oct. 2002, pp. 1216-1223.
DeRubeis RJ et al Cognitive therapy vs Medications in the treatment of moderate to severe depression Arch Gen Psychiatry 2005; 62:409-416.
Drake RE et al Suicide attempts associated with akathisia Am J Psychiatry 142:4, Apr. 1985.
English translation of Statement of Claim submitted in the opposition of counterpart Israeli Office Action application No. 169358 dated Dec. 1, 2013.
Evins at al. Buprorion and smoking cessation (Am. J. Psychiatry 156:5, May 1999 pp. 798-799.).
Ferris RM et at Buproprion: a new antidepressant drug, the mechanism of action of which is not associated with downregulation of postsynaptic-adrenergic, serotonergic (5-HT2), a2-adrenergic, imipramine and dopaminergic receptors in brain. Neurophartnacology 22 No. II, 1257-1267, 1983.
George, T. et al., "A Placebo-Controlled Trial of Bupropion for Smoking Cessation in Schizophrenia" (2002) Biological Psychiatry, vol. 52, pp. 53-61.
Goldapple K. et al Modulation of cortical-limbic pathways in major depression. Arch. Gen Psychiatry, vol. 61, Jan. 2004, pp. 34-41.
Goodman et al., "The Pharmacological Basis of Therapeutics", 2001, vol. ed. 10, p. 451 and p. 468.
Gordon et al., Mood Stabilization and weight loss with topiramate; http://proquest.umi.com/pqdlink?index=40&did-00000004224763&SrchMode=3&sid=28 . . . .
Harvey, Anne T., et al., "Evidence of the Dual Mechanisms of Action of Venlafaxine", Arch Gen Psychiatry, vol. 57, May 2000, 503-509.

Hirose S et al. An open pilot study combining risperidone and a selective serotonin reuptake inhibitor as initial antidepressant therapy. J. Clin Psychiatry vol. 63, (8) Aug. 2002, pp. 733-736.
Hirose, Shigehiro M. D., et al., "An Open Piot Study Combining Risperidone and a Selective Serotonin Reuptake Inhibitor as Inital Antidepressant Therapy", J. Clin. Phsychiatry, Aug. 2002, vol. 68 (8), p. 733-736.
Hirsch SR et al The concept and efficacy of the treatment of parasuicide. Br J. clin Partnac 1983, 15, 189S-194S table 1 on p. I895.
Interview with Robert Temple diractor of FDA's Office of Medical Policy—Pittsburgh Post-Gazette Dec. 14, 2006 (FDA may expand alert . . . ).
Interview with Hussei Katz director of neuropnarmacological drug products at the FDA—Tribune Review Mar. 23, 2004 (Antidepressants . . . ).
Jacobsen, Risperidone in the Treatment of Affective Illness and Obsessive-Compulsive Disorder, Journal of Clinical Psychiatry, 1995, vol. 56, No. 9, pp. 423-429.
Jambur Ananth; "Treatment-Resistant Depression"; Psychother Psychosom; 1998; pp. 61-70; 67; S. Karger AG, Basel, Switzerland.
Japanese Office Action dated Apr. 16, 2008.
Kalkman, Hans O., "The role of $\alpha$2-adrenoceptor antagonism in the anti-cataleptic properties of the atypical neuroleptic agent, clozapine, in the rate", British Journal of Pharmacology, 1998, vol. 124, p. 1550-1556.
Kelleher et al., "Advances in Atypical Antipsychotics for the Treatment of Schizophrenia" CNS Drugs (2002) Vol .16, No. 4, pp. 249-261.
Burris, Kevin D., et al., Aripiprazole, a Novel Antipsychotic, Is a High-Affinity Partial Agonist at Human Dopamine D2 Receptors, The Journal of Pharmacology and Experimental Therapeutics, 2002, vol. 302, No. 1, pp. 381-389.
Konig F., et al. "First Experiences in Combination Therapy Using Olanzapine with SSRIs (Citalopram, Parozetine in Delusional Depression", Neuropsychobiology, 2001, vol. 43(3), p. 170-174.
Kowatch, Robert A., et al., The Use of Mood Stabilizers and Atypical Antipsychotics in Children and Adolescents With Bipolar Disorders, CNS Spectrums, 2003, vol. 8, No. 4, pp. 273-280.
Kramer MS et al The effects of a selective D4 dopamine receptor antagonist (L-745,870) in acutely psychotic inpatients with schizophrenia. Arch Gen Psychiatry 1997; 54:567-572.
Kuoppamaki M et al Differential regulation of rat 5-HT2A and 5-HT2C receptors after chronic treatment with clozapine, chrorpromazine and three putative atypical antipsychotic drugs. Neuropsychopharmacology I 3:139-150, 1995.
Landen M. et at A randomized, double-blind, placebo-controlled trial of buspirone in combination with an SSRI in patients with treatment-refractory depression. J. Clin Psychiatry 1998; 59:664-668.
Lawler C. P. et al, "Interactions of the Novel Antipsychotic Aripiprazole (OPC-14597) with Dopamine and Serotonin Receptor Subtypes," Neuropsychopharmacology, 1999, vol. 20, No. 6. pp. 612-627.
Linner, Love, et al., "Noradrenaline Reuptake Inhibition Enhances the Antipsychotic-like Effect of Raclopride and Potentiates $D_2$-blockage-induced Dopamine Release in the medial Prefrontal Cortex of the Rat", Neuropsychopharmacology, 2002, vol. 27(5), p. 691-698 (D167).
Lipinski J F. et al Fluoxetine-induced akathisia: Clinical and theoretical implications. J Clin Psychiatry 50:9 1989 339-342.).
Marangell, Lauren B., "Olanzapine in the Treatment of Apathy in Previously Depressed Participants Maintained With Selective Serotonin Reuptake Inhibitors: An Open-Label, Flexible-Dose Study", J. Clin. Psychiatry, May 2002 vol. 63 (5), p. 391-395.
Mark W. Viner, M.D. et al.; "Low-dose Risperidone Augmentation of Antidepressants in Nonpsychotic Depressive Disorders with Suicidal Ideation"; Journal of Clinical Psychopharmacology; Feb. 2003; pp. 104-106: vol. 23. No. I: Lippincott Williams & Wilkins: Philadelphia, Pennsylvania.
Marshall, et al., Bupropion and sertraline combination treatment in refractory depression, J. Psychopharmacology, 1995, vol. 9, No. 3, pp. 284-286.

(56) References Cited

OTHER PUBLICATIONS

McElroy, et al., Clozapine in the Treatment of Psychotic Mood Disorders, Schizoaffective Disorder, and Schizophrenia, Journal of Clinical Psychiatry, 1991, vol. 52, No. 10. pp. 411-414.
Meltzer, et al., Psychopharmacology, The Third Generation of Progress, 1987, pp. 1021-1029 and 1031-1049.
Merck Index. 12th edition, p. 1062 (1996 published).
Michael E. Thase, M.D.; "What Role Do Atypical Antipsychotic Drugs Have in Treatment-Resistant Depression?"; The Journal of Clinical Psychiatry: Feb. 2002; pp. 95-103; 63:2; Physicians Postgraduate Press, Inc.. Memphis, Tennessee.
Möller, et al., Treatment of Bipolar Disorder, J. Clin. Psychiatry, 2003, vol. 64, suppl. 6, pp. 9-17.
Montgomery SA et al Br J. clin Parmac 1983, 15, 183S-188S, p. 183S second column second paragraph, and p185S first column third paragraph.
Morpurgo, Clara, "Drug-Induced Modifications of Discriminated Avoidance Behavior in Rats", Psychopharmacology (Berl.) vol. 8: p. 91-99 (1965).
Nair, NPV et al Neurochemical and receptor theories of depression. Psychiat J. Univ Ottava, vol. 14(2) 1989 pp. 328-341 p. 328 first column lines 3-5 and 9-10.).
Narendran, Rajesh, et al., "Olanzapine Therapy in Treatment-Resistant Psychotic Mood Disorders: A Long-Term Follow-Up Study", J. Clin. Psychiatry, Jul. 2001, vol. 62(7), p. 509-516.
Nelson, Overcoming Treatment Resistance in Depression, Journal of Clinical Psychiatry, 1998, vol. 59, suppl. 16, pp. 13-19.
Nemeroff, Charles, B., Augmentation Strategies in Patients with Refractory Depression, Depression and Anxiety, 1996-1997, vol. 4, No. 4, pp. 169-181.
O'Connor, Adding Risperidone to Selective Serotonin Reuptake Inhibitor Improves Chronic Depression, Journal of Clinical Psychopharmacology, 1998, vol. 18, No. 1, pp. 89-91.
Office Action for Indian Application No. 3698/KOLNP/2007.
Ost. et al., "Probability rating in claustrophobic patients and normal controls" Behavior Research and Therapy (2000) vol. 38 pp. 1107-1116.
Ostroff, Robert B. et al, "Risperidone Augmentation of Selective Serotonin Reuptake Inhibitors in Major Depression", J. Clin. Psychiatry, 1999, vol. 60 (4), (Apr.), p. 256-259.
Owens M.H., Abstract, Escitalopram:a second generation SSRI, CNS Spectr, Apr. 7, 2002, 34-39.
Patient Leaflet of Abilify ("Enclosure") (Publication date unidentified), 2002, Otsuka Pharmaceutical Co, Ltd, Tokyo, 101-8535 Japan.
Paton, C. Generic clozapine: outcomes after switching formulations. British Journal of Psychiatry 2006. 189 184-185.
Perez V et at A double-bind, randomized, placebo-controlled trial of pindolol augmentation in depressive patients resistant to serotonin reuptake inhibitors. Arch Gen Psychiatry. 1999; 56(4):375-379.
Pivac et al., "Collegium Internationale Neuro-Psychopharmacologicum" Psychiatria Danubina (2002) vol. 14, No. 3-4, pp. 231-242.
Plaroum F et al Marked reduction in indexes of dopamine metabolism among patients with depression who attempts suicide. Arch Gen Psychiatry 49, 1992 447-450. p. 447 last two lines of first column and first two of second one, and p. 448 last four lines of second column.
Poyurovsky M., et al., Mirtazapine for the neuroleptic-induced akathisia. Am J Psychiatry 158:5 2001 p. 8I9 second paragraph first sentence.
Printout of US pre-grant publication 2003/0049308 (Theobald et al.).
Reeves H. et al., Efficacy of risperidone augmentation to antidepressants in the management of suicidality in major depressive disorder: a randomized, double-blind, placebo-controlled study. J. Clin Psychiatry 69:Aug. 8, 2008).
Reeves H et al, Efficacy of risperidone augmentation to antidepressants in the management of suicidality in major depressive disorder: a randomized, double-blind, placebo-controlled pilot study. J Clin Psychiatry 69:8 2008 1228-1236. page 1229 first col. 9-10.
Reynolds, Gavin P., et al., "New Approaches to the Drug Treatment of Schizophrenia", Advances in Pharmacology, 1995: vol. 32,: p. 461-503.
Robertson et al., "Major Tranquilizers Used as Antidepressants" Journal of Affective Disorders (1982) vol. 4, pp. 173-193.
Roth, B.L. et al., Chronic mianserine treatment decreases 5-HT2 receptor binding without altering 5-HT2 receptor mRNA levels. European Journal of Pharmacology—Molecular Pharmacology Section, 207 (1991) 169-172.
Roth et al., "D4 Dopamine receptor binding affinity does not distinguish between typical and atypical antipsychotic drugs," Psychopharmacology (1995) vol. 120, pp. 365-368.
Rothschild, Management of Psychotic Treatment-Resistant Depression, The Psychiatric Clinics of North America, 1996, vol. 19, No. 2, pp. 237-252.
Roy, A. et al., "Marked Reduction in Indexes of Dopamine Metabolism Among Patients With Depression Who Attempt Suicide", Arc Gen Psychiatry 49, 1992, 447-450.
Saxena, et al., Risperidone Augmentation of SRI Treatment for Refractory Obsessive-Compulsive Disorder, J. Clin. Psychiatry, 1996, vol. 57, pp. 303-306.
Schmidt et al., "Ziprasidone: a novel antipsychotic agent with a unique human receptor binding profile" European Journal of Pharmacology (2001) vol. 425, pp. 197-201.
Sharp, D.M. et al., Global measures of outcome in controlled comparison of pharmacological and psychological treatment of panic disorder and agoraphobia in primary care. Br J Gen Pract 1997 47(416) 150-5.
Shaw. E.D., et al., A case of suicidal and homicidal ideation and akathisia in a double-blind neuroleptic crossover study J clin psychopharrnacol vol. 6(3) 1986 196-197.
Shear, M.K. e al Suicide associated with akathisia and depot fluphenazine treatment. Journal of Clinical Psychopharmacology vol. 3(4) 1983 235-236.
Preskorn, Sheldon H., Relating Clinical Trials to Psychiatric Practice: Part I: The Case of a 13-Year Old on Aripiprazole and Fluoxetine, Journal of Psychiatric Practice, 2003, vol. 9, No. 4, pp. 307-313.
Shelton, et al., A Novel Augmentation Strategy for Treating Resistant Major Depression, American Journal of Psychiatry, 2001, vol. 158, No. 1, pp. 131-134.
Shigehiro Hirose, M.D. and Charles R. Ashby, Jr., Ph.D.; "An Open Pilot Study Combining Risperidone and a Selective Serotonin Reuptake Inhibitor as Initial Antidepressant Therapy"; Journal of Clinical Psychiatry; Aug. 2002; pp. 733-736; 63:8; Physicians Postgraduate Press, Inc., Memphis, TN.
Simon NM et al (Longitudinal outcome with pharmacotherapy in a naturalistic study of panic disorder. Journal of Affective Disorders 69 (2002) 201-208.
Smith WT et al. Short term augmentation of fluoxetine with clonazepam in the treatment of depression: A double-blind study. Am J Psychiatry 155:10 1998 1339-45.
Souery, D. et al.; "Treatment resistant depression: methodological-overview and operational criteria"; European Neuropsychopharmacology; 1999; pp. 83-91; 9; Elsevier Science B.V./ECNP; Amsterdam, The Netherlands.
Steiner, M., "The neurochemistry of mood", Psychiat J. Univ Ottava, vol. 14(2) 1989 pp. 342-343. p. 342 first column lines 5-8.
Stoner, S.C., et al., A program to convert patients from Trade-name to generic clozapine Pharmacotherapy 2003; 23(6):806-810 [particularly p. 806 second column 3rd line from the bottom on patent expiration.
Stuart et al., "Escitalopram (S-Enantiomer of Citalopram): Clinical Efficacy and Onset of Action Predicted from a Rat Model", Pharmacology and Toxicology, 2001, vol. 88, pp. 282-286.
Tang et al., PNU-96415E, a Potential Antipsychotic Agent with Clozapine-Like Pharmacological Properties The Journal of Pharmacology and Experimental Therapeutics (1997) vol. 281, pp. 440-447.
Tarazi et al., Long-term effects of olanzapine, risperidone, and quetiapine on serotonin 1A, 2A and 2C receptors in rat forebrain regions; XP-002475772; Psychopharmacology (2002) 161:263-270.
Thase, Michael E., M.D.; "What Role Do Atypical Antipsychotic Drugs Have in Treatment-Resistant Depression?"; The Journal of

(56) References Cited

OTHER PUBLICATIONS

Clinical Psychiatry: Feb. 2002; pp. 95-103; 63:2; Physicians Postgraduate 'Press, Inc. Memphis, Tennessee.
The Merck Manual of Diagnosis and Therapy, Seventeenth Edition, published 1999 by Merck Research Laboratories, ed. By Beers and Berkow, pp. 1531-1538 and 1569-1570.
Therapie, 1999, vol. 54, No. 2, pp. 267-269.
Tohen et al; Efficacy of Olanzapine in Combination With Valproate or Lithium in the Treatment of Mania in Patients Partially Nonresponsive to Valproate or Lithium Monotherapy; XP009092539; Arch Gen Psychiatary; vol. 59; Jan. 2002, pp. 62-69.
Tohen, et al., Olanzapine versus placebo in the treatment of acute mania, Eur. Neuropsychopharmacol., 1998, vol. 8, No. suppl. 2, s178.
Tollefson GD et al (1998a) Depressive signs and symptoms in Schizophrenia. A prospective blinded trial of olanzapine and haloperidol. Arch Gen Psychiatry 998; 55:250-258.
Tollefson GD et al (1998b) A double-blind, controlled comparison of the novel antipsychotic olanzapine versus haloperidol or placebo on anxious and depressive symptoms accompanying schizophrenia. Biol Psychiatry 1998; 43:803-810.
Toth M., et al, Antagoist-mediated down-regulation of 5-hydroxytryptamine type 2 receptor gene expression: modulation of transcription. Molecular pharmacology 45:1095-110, 1994.
Trivedi, M. H., et al., "Clinical Results for Patients with Major Depressive Disorder in the Texas Medication Algorithm Project", Arch. Gen. Psychiatry, vol. 61, Jul. 2004 p. 669-680.
Tsai G E. A new class of antipsychotic drugs enhancing neurotransmission by NMDA receptors Psychiatric Times Dec. 2008, p. 16-18.
Uhlenhuth et al., The revised Anxious Thoughts and Tendencies (AT&T) scale: a general measure of anxiety-prone cognitive style Journal of Affective Disorders (1999) vol. 52, pp. 51-58.
Van Putten T. et al., "Behavoral toxicity of antipsychotic drugs", J Clin Psychiatry 48 [9, Suppl]:13-19, 1987.
Van Putten T., "The many faces of akathisia" Comprehensive Psychiatry vol. 16 (1) 1975 43-47.
Viner MW et al Low-dose risperidone augmentation of antidepressants in nonpsychotic depressive disorders with suicidal ideation. Journal of Clinical Psychopharmacology 23:1 2003).

Weisler, et al., Adjunctive Use of Olanzapine in Mood Disorders: Five Case Reports, Annals of Clinical Psychiatry, 1997, vol. 9, No. 4, pp. 259-262.
WHfoods, Is Fruit Juice as good as whole fruit published online at http://www.whfoods.com/genpage.php?tname=george&dbid=74 Aug. 25, 2008.
White, et al., Seizure Resulting from a Venlafazine Overdose, The Annals of Pharmacotherapy, 1978, vol. 31, No. 2, pp. 178-180.
Winnans, E., "Aripiprazole" American Journal of Health-System and Pharmacy, vol. 60, Dec. 1, 2003, pp. 2437-2445.
Wolfersdorf, et al., Paroxetine as Antidepressant in Combined Antidepressant-neuroleptic Therapy in Delusional Depression: Observation of Clinical Use, Pharmacopsychiatry, 1995, vol. 28, No. 2, pp. 56-60.
Wolfersdorf, et al., Pharmacotherapy of Delusional Depression: Experience with Combinations of Antidepressants with the Neuroleptics Zotepine and Haloperidol, Neuropsychobiology, 1994, vol. 29, pp. 189-193.
Worthington, et al., Aripiprazole as an Augmentor of SSRIs in Mood and Anxiety Disorders Patients, American Psychiatric Association 2003 Annual Meeting, May 17-22, 2003 (poster, May 19, 2003) (summary of the abstract, May 17, 2003) (meeting program, May 17, 2003).
Zubenko G et al Antidepressant-related akathisia J Clin Psychopharmacol vol. 7(4) 1987 254-257.
Bandelow et al., Aripiprazole, a "Dopamine-Serotonin System Stabilizer" in the treatment of Psychosis; XP009098592; ISSN 1443-1055, Mar. 23, 2003.
Gordon et al., Mood Stabilization and weight loss with topiramate; Jun. 1999; 156(6):968-9.
Second Expert Opinion of Prof. Paul Harrison in the Opposition of counterpart Israeli Application No. 169358, dated Dec. 8, 2015, including appendices.
Expert Opinion of Michael E. Thase, M.D. in the Opposition of counterpart Israeli Application No. 159358, dated Jun. 23, 2015, including appendices.
Expert Opinion of Prof. Avi Weizmann in the Opposition of counterpart Israeli Application No. 169358, including appendices.
Request by Applicant in Respect of Opponent's Evidence-in-Reply, in the Opposition of counterpart Israeli Application No. 169358, dated Jan. 2016.

* cited by examiner under exploration based on the idea that the combination of an atypical antipsychotic drug that act as a dopamine-serotonin system stabilizer with a serotonin reuptake inhibitor, which is thought to be an unreasonable combination from the prior art, would show effective therapeutic effects to such mood disorders as depression and major depressive disorder, without evoking serious side-effects associated with other antipsychotic drugs.

CARBOSTYRIL DERIVATIVES AND SEROTONIN REUPTAKE INHIBITORS FOR TREATMENT OF MOOD DISORDERS

This is a Divisional of application Ser. No. 10/540,577 filed Dec. 16, 2005, claiming priority based on Japanese Patent Application No. 2002-379003 filed Dec. 27, 2002, the contents of all of which are incorporated herein by reference in their entirety.

TECHNICAL FIELD

The present invention provides pharmaceutical compositions comprising carbostyril derivatives that act as dopamine-serotonin system stabilizers in combination with serotonin reuptake inhibitors in a pharmaceutically acceptable carrier. Further, the present invention provides methods of using the compositions of the present invention to treat mood disorders such as depression and major depressive disorder.

BACKGROUND ART

The number of people with mood disorders such as major depressive disorder, and exhibiting various symptoms of depressions is increasing every year for numerous reasons such as social stress, unemployment, disease, and poverty. Depression is a major social problem throughout the world. For example, in Japan the occurrence rate of depression in the generation older than 65 years is 5% or more, including major depressive disorder. Some of the depression in this population is associated with mental disturbances representing senile diseases associated with dementia and neurosis. Many depressed patients show high recurrence rate, and severe depressive symptoms are major causes of suicide and drug abuse (Nishimura Ken, "NIPPON RONEN IGAKU-ZASSHI", Vol. 33, pp 503-504 (1996)).

Since the period of 1950, tricyclic antidepressant drugs (e.g., imipramine, desipramine, amitriptyline, etc.) have been developed that act to inhibit monoamine reuptake. They are frequently used for treating patients suffering from mood disorders, such as depression and major depressive disorder. However, these drugs have side-effects such as the following: dry mouth, hazy eyes, dysuria, constipation, recognition disturbance and the like due to anticholinergic activity; cardiovascular side-effects such as, orthostatic hypotension, tachycardia and the like on the basis of $\alpha_1$-adrenoreceptor antagonist activity; side-effects such as, sedation, increase in the body weight and the like on the basis of histamine-$H_1$ receptor antagonist activity.

Since 1980, serotonin reuptake inhibitors have been developed, including but not limited to fluoxetine, duloxetine, venlafaxine, milnacipran, citalopram, escitalopram, fluvoxamine, paroxetine and sertraline, and these inhibitors have side-effects such as recognition disturbance, sleep disturbance, and excerbation of anxiety and agitation. Additionally, these inhibitors also have other side effects in the digestive organs, such as nausea, vomiting and the like.

For the reason that the mood disorders such as depressive symptoms, depression and the like are diseases with severely strong psychalgia, the manifestation of new symptoms on the basis of these side-effects are quite serious problems in the therapy of mood disorders (Shioe Kunihiko, Kariya Tetsuhiko, "SHINKEI SEISHIN YAKURI", Vol. 11, pp 37-48 (1989); Yamada Mitsuhiko, Ueshima Kunitoshi, "RINSHOU SEISHIN YAKURI", Vol. 1, pp 355-363 (1998)).

Although the mood disorders including depression and major depressive disorder are heterogeneous diseases, and the causes of these diseases are not been fully understood, it is likely that the abnormalities of monoaminergic central nervous system caused by serotonin, norepinephrine and dopamine and the like, and the abnormality of various hormones and peptides as well as various stressors are causes of depression and various mood disorders (Kubota Masaharu et al., "RINSHOU SEISHIN IGAKU", Vol. 29, pp 891-899 (2000)). For these reasons, even though antidepressant drugs, such as tricyclic antidepressants and serotonin reuptake inhibitors were used, these drugs are not always effective in treating all depressed patients. About 30% of the depressed patients do not respond to the primarily selected antidepressants (Nelson, J. C, et al., J. Clin. Psychiatry, 55, pp 12-19 (1994)). Further, when a second or third antidepressant is administered to these patients, insufficient improvements of the symptoms occurs in about 10% of these patients (Inoeu Takeshi, Koyama Tsukasa, "RINSHOU SEISHIN IGAKU", Vol. 38, pp 868-870 (1996)). These patients are called as refractory depression patients.

In some cases, electric shock therapy is used to treat refractory depression, and the efficacy of this treatment has been reported. However, in fact, the condition of numerous patients is not improved (Inoue Takeshi, Koyama Tsukasa, "RINSHOU SEISHIN YAKURI", Vol. 2, pp 979-984 (1999)). Additionally, psychological anguish experienced by these patients and their families concerning the use of the electric shock therapy can be severe.

New therapeutic trials involve proposed combined therapies using an atypical antipsychotic drug, such as olanzapine, which is an agent for treating for schizophrenia (antipsychotic drug), together with an antidepressant drug such as serotonin reuptake inhibitor (EP 0 367 141, WO 98/11897, WO99/61027, WO99/62522, U.S. 2002/0123490A1 and the like). However, commercially available atypical antipsychotic drugs have significant problems relating to their safety. For example, clozapine, olanzapine and quetiapine increase body weight and enhance the risk of diabetes mellitus (Newcomer, J. W. (Supervised Translated by Aoba Anri), "RINSHOU SEISHIN YAKURI", Vol. 5, pp 911-925 (2002); Haupt, D. W. and Newcomer, J. W (Translated by Fuji Yasuo and Misawa Fuminari), "RINSHOU SEISHIN YAKURI", Vol. 5, pp 1063-1082 (2002)). In fact, urgent safety alerts have been issued in Japan relating to hyperglycemia, diabetic ketoacidosis and diabetic coma caused by olanzapine and quetiapine, indicating that these drugs were subjected to dosage contraindication to the patients with diabetes mellitus and patients having anamnesis of diabetes mellitus. Risperidone causes increases serum prolactin levels and produces extrapyramidal side effects at high dosages. Ziprasidone enhances the risk of severe arrhythmia on the basis of cardio-QTc prolongation action. Further, clozapine induces agranulocytosis, so that clinical use thereof is strictly restricted (van Kammen, D. P. (Compiled under Supervision by Murasaki Mitsuroh), "RINSHOU SEISHIN YAKURI", Vol. 4, pp 483-492 (2001)).

Accordingly what is needed are new compositions useful for treating mood disorders, particularly, depression and major depressive disorder, which are efficacious and do not cause the deleterious side effects associated with prior art compounds.

DISCLOSURE OF THE INVENTION

The present invention solves the problem described above by providing novel compositions and methods of using these compositions for treating mood disorders, particularly depression and major depressive disorder.

The present invention provides solutions to the above-mentioned problems, and demonstrates that the mood disorders such as depression, major depressive and the like can be treated effectively by administering to a patient with such disorder a pharmaceutical composition comprising at least one carbostyril derivative that is a dopamine-serotonin system stabilizer in combination with at least one serotonin reuptake inhibitor in a pharmaceutically acceptable carrier.

A preferred carbostyril derivative of the present invention that is a dopamine-serotonin system stabilizer is aripiprazole or a metabolite thereof. Another preferred carbostyril derivative of the present invention that is a dopamine-serotonin system stabilizer is a metabolite of aripiprazole called dehydroaripiprazole, also known as OPC-14857. Other such metabolites of aripiprazole included within the present invention are shown in FIG. 8. Preferred metabolites are shown in FIG. 8 indicated by the following designations: OPC-14857, DM-1458, DM-1451, DM-1452, DM-1454 and DCPP.

Aripiprazole, also called 7-{4-[4-(2,3-dichlorophenyl)-1-piperazinyl]butoxy}-3,4-dihydro-2(1H)-quinolinone, is a carbostyril compound and is useful for treating schizophrenia (EP 0 367 141, U.S. Pat. No. 5,006,528). Aripiprazole is also known as 7-{4-[4-(2,3-dichlorophenyl)-1-piperazinyl]butoxy}-3,4-dihydrocarbostyril, Abilify, OPC-14597, OPC-31 and BMS-337039. Aripiprazole possesses 5-HT1A receptor agonist activity, and is known as useful compound for treating types of depression and refractory depressions, such as endogeneous depression, major depression, melancholia and the like (WO 02/060423, U.S. Patent Application 2002/0173513A1). Aripiprazole has activity as an agonist at the serotonin receptors and dopamine receptors, and acts as an agonist or partial agonist at the serotonin 5-HT1A receptor and as an agonist or partial agonist at the dopamine $D_2$ receptor. Aripiprazole is a dopamine-serotonin system stabilizer. Metabolites of aripiprazole are included within the scope of the present invention. One such metabolite of aripiprazole is called dehydroaripiprazole. Other such metabolites of aripiprazole included within the present invention are shown in FIG. 8. Preferred metabolites are shown in FIG. 8 indicated by the following designations: OPC-14857, DM-1458, DM-1451, DM-1452, DM-1454 and DCPP.

The at least one serotonin reuptake inhibitor used in the present invention includes but is not limited to the following: fluoxetine, duloxetine, venlafaxine, milnacipran, citalopram, fluvoxamine, paroxetine, sertraline, escitalopram and salts thereof. In a preferred embodiment, the pharmaceutical composition comprises aripiprazole and citalopram in a pharmaceutically acceptable carrier.

The novel compositions of present invention comprising at least one carbostyril derivative with activity as a dopamine-serotonin system stabilizer and at least one serotonin reuptake inhibitor in a pharmaceutically acceptable carrier may be combined in one dosage form, for example a pill. Alternatively the at least one carbostyril derivative with activity as a dopamine-serotonin system stabilizer and the at least one serotonin reuptake inhibitor may be in separate dosage forms, each in a pharmaceutically acceptable carrier. These compositions are administered to a patient with a mood disorder, particularly depression or major depressive disorder, in an amount and dosage regimen effective to treat the mood disorder.

Accordingly, it is an object of the present invention to provide a pharmaceutical composition useful for treating a mood disorder.

It is an object of the present invention to provide a composition useful for treating a mood disorder, wherein the mood disorder is depression or major depressive disorder.

It is another object of the present invention to provide a composition comprising at least one carbostyril derivative with activity as a dopamine-serotonin system stabilizer and at least one serotonin reuptake inhibitor in a pharmaceutically acceptable carrier.

Yet another object of the present invention is to provide a composition comprising at least one carbostyril derivative with activity as a dopamine-serotonin system stabilizer and at least one serotonin reuptake inhibitor in a pharmaceutically acceptable carrier, wherein the carbostyril derivative is aripiprazole or a metabolite thereof.

Yet another object of the present invention is to provide a composition comprising at least one carbostyril derivative with activity as a dopamine-serotonin system stabilizer and at least one serotonin reuptake inhibitor in a pharmaceutically acceptable carrier, wherein the carbostyril derivative is aripiprazole and the serotonin reuptake inhibitor is citalopram.

Yet another object of the present invention is to provide a composition comprising at least one carbostyril derivative with activity as a dopamine-serotonin system stabilizer and at least one serotonin reuptake inhibitor, wherein the carbostyril derivative with activity as a dopamine-serotonin system stabilizer is a metabolite of aripiprazole and is dehydroaripiprazole (OPC-14857), DM-1458, DM-1451, DM-1452, DM-1454 or DCPP.

Yet another object of the present invention is to provide a composition comprising at least one carbostyril derivative with activity as a dopamine-serotonin system stabilizer and at least one serotonin reuptake inhibitor, wherein the carbostyril derivative is dehydroaripiprazole.

It is an object of the present invention to provide a use of a composition useful for treating a mood disorder in the preparation of a medicament for treatment of a mood disorder, wherein the mood disorder is depression or major depressive disorder.

It is another object of the present invention to provide a use of a composition comprising at least one carbostyril derivative with activity as a dopamine-serotonin system stabilizer and at least one serotonin reuptake inhibitor in a pharmaceutically acceptable carrier in the preparation of a medicament for treatment of a mood disorder.

Yet another object of the present invention is to provide a use of a composition comprising a carbostyril derivative with activity as a dopamine-serotonin system stabilizer and at least one serotonin reuptake inhibitor in a pharmaceutically acceptable carrier in the preparation of a medicament for treatment of mood disorders, wherein the carbostyril derivative is aripiprazole or a metabolite thereof.

Yet another object of the present invention is to provide a use of a composition comprising a carbostyril derivative with activity as a dopamine-serotonin system stabilizer and at least one serotonin reuptake inhibitor in a pharmaceutically acceptable carrier in the preparation of a medicament for treatment of mood disorders, wherein at least one carbostyril derivative is aripiprazole and at least one serotonin reuptake inhibitor is citalopram.

Yet another object of the present invention is to provide a use of a composition comprising at least one carbostyril derivative with activity as a dopamine-serotonin system stabilizer and at least one serotonin reuptake inhibitor pharmaceutically acceptable carrier in the preparation of a medicament for treatment of mood disorders, wherein the carbostyril derivative with activity as a dopamine-serotonin system stabilizer is a metabolite of aripiprazole and is dehydroaripiprazole (OPC-14857), DM-1458, DM-1451, DM-1452, DM-1454 or DCPP.

Yet another object of the present invention is to provide a use of a composition comprising a carbostyril derivative with activity as a dopamine-serotonin system stabilizer and at least one serotonin reuptake inhibitor in a pharmaceutically acceptable carrier in the preparation of a medicament for treatment of mood disorders, wherein the carbostyril derivative is dehydroaripiprazole.

It is an object of the present invention to provide a method for treating a mood disorder.

It is an object of the present invention to provide a method for treating a mood disorder wherein the mood disorder is depression or major depressive disorder.

It is another object of the present invention to provide a method for treating a mood disorder comprising administration to a patient with a mood disorder of a composition comprising at least one carbostyril derivative with activity as a dopamine-serotonin system stabilizer and at least one serotonin reuptake inhibitor in a pharmaceutically acceptable carrier.

It is another object of the present invention to provide a method for treating a mood disorder comprising administration to a patient with a mood disorder of a composition comprising at least one carbostyril derivative with activity as a dopamine-serotonin system stabilizer and at least one serotonin reuptake inhibitor together in a pharmaceutically acceptable carrier, wherein the carbostyril derivative is aripiprazole or a metabolite thereof.

It is another object of the present invention to provide a method for treating major depressive disorder comprising administration to a patient with major depressive disorder of a composition comprising a carbostyril derivative with activity as a dopamine-serotonin system stabilizer and at least one serotonin reuptake inhibitor together with a pharmaceutically acceptable carrier, wherein the carbostyril derivative is aripiprazole and the serotonin reuptake inhibitor is citalopram.

Still another object of the present invention is to provide a method for treating a mood disorder comprising administration to a patient with a mood disorder of a composition comprising at least one carbostyril derivative with activity as a dopamine-serotonin system stabilizer and at least one serotonin reuptake inhibitor in a pharmaceutically acceptable carrier, wherein the carbostyril derivative is a metabolite of aripiprazole and is dehydroaripiprazole (OPC-14857), DM-1458, DM-1451, DM-1452, DM-1454 or DCPP.

Yet another object of the present invention is to provide a method for treating major depressive disorder comprising administration to a patient with major depressive disorder of a composition comprising at least one carbostyril derivative with activity as a dopamine-serotonin system stabilizer and at least one serotonin reuptake inhibitor in a pharmaceutically acceptable carrier, wherein the mood disorder is major depressive disorder.

It is another object of the present invention to provide a method for treating major depressive disorder comprising administration to a patient with major depressive disorder of a composition comprising at least one carbostyril derivative with activity as a dopamine-serotonin system stabilizer and at least one serotonin reuptake inhibitor in a pharmaceutically acceptable carrier.

It is another object of the present invention to provide a method for treating major depressive disorder comprising administration to a patient with major depressive disorder of a composition comprising at least one carbostyril derivative with activity as a dopamine-serotonin system stabilizer and at least one serotonin reuptake inhibitor together with a pharmaceutically acceptable carrier, wherein the carbostyril derivative is aripiprazole or a metabolite thereof.

Still another object of the present invention is to provide a method for treating major depressive disorder comprising administration to a patient with major depressive disorder of a composition comprising at least one carbostyril derivative with activity as a dopamine-serotonin system stabilizer and at least one serotonin reuptake inhibitor in a pharmaceutically acceptable carrier, wherein the carbostyril derivative is a metabolite of aripiprazole and is dehydroaripiprazole (OPC-14857), DM-1458, DM-1451, DM-1452, DM-1454 or DCPP.

These and other objects, advantages, and uses of the present invention will reveal themselves to one of ordinary skill in the art after reading the detailed description of the preferred embodiments and the attached claims.

DETAILED DESCRIPTION OF THE INVENTION

Figure 1:
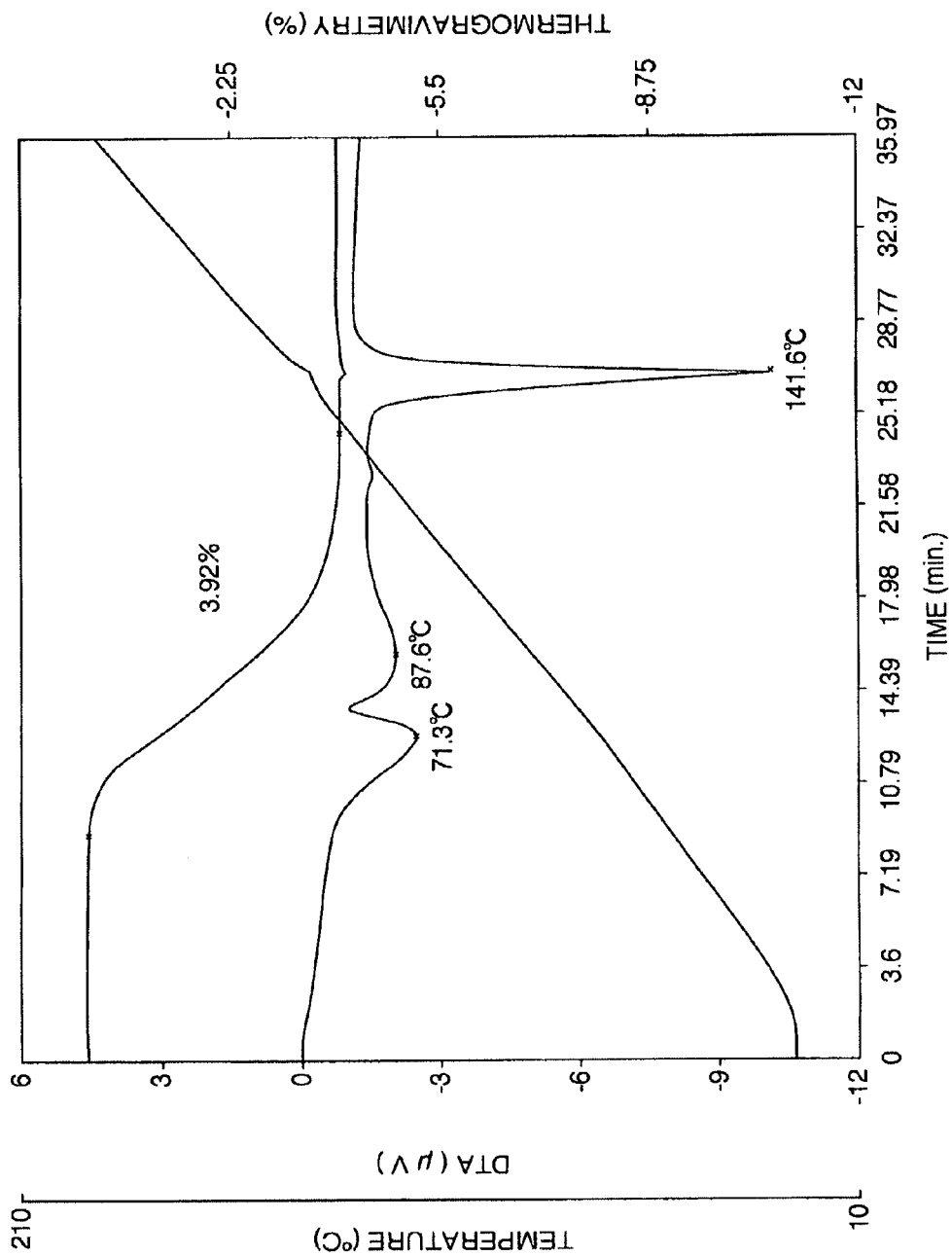
FIG. 1 is the thermogravimetric/differential thermogram of the aripiprazole hydrate A obtained in Reference Example 4.

The pharmaceutical composition of the present invention comprises a first ingredient comprising a carbostyril derivative active as a dopamine-serotonin system stabilizer and a second ingredient comprising a serotonin reuptake inhibitor, in a pharmaceutically acceptable carrier. The pharmaceutical compositions of the present invention are useful in treating mood disorders, including depression and major depressive disorder.

The Pharmaceutical Composition: The First Ingredient

The first ingredient comprises a carbostyril derivative active as a dopamine-serotonin system stabilizer. Such carbostyril derivative has activity as an agonist or partial agonist at some serotonin receptors and some dopamine receptors, preferably as an agonist or partial agonist at the serotonin 5-HT1A receptor and as an agonist or partial agonist at the dopamine $D_2$ receptor. Carbostyril derivatives are described in U.S. Pat. No. 5,006,528 and U.S. published patent application 2002/0173513A1. In one embodiment of the present invention, the carbostyril derivatives represented by the following formula (1) are used:

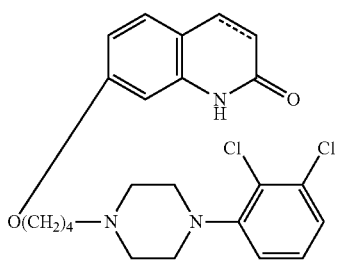

wherein the carbon-carbon bond between 3- and 4-positions in the carbostyril skeleton is a single or a double bond.

In a preferred embodiment, this activity of the carbostyril derivative is as an agonist or partial agonist at the 5-HT1A receptor and an agonist or partial agonist at the dopamine $D_2$ receptor subtype. In another preferred embodiment, the carbostyril derivative to be used as a first component in the present invention is aripiprazole, or a metabolic derivative thereof. Metabolic derivatives of aripiprazole include but are not limited to dehydroaripiprazole, also called OPC-14857. Other metabolic derivatives of aripiprazole include but are not limited to the chemical structures shown in FIG. 8 as OPC-14857, DM-1458, DM-1451, DM-1452, DM-1454 and DCPP. All of the aforementioned carbostyril derivatives may be used as a first component in the practice of the present invention.

Aripiprazole, also called 7-{4-[4-(2,3-dichlorophenyl)-1-piperazinyl]butoxy}-3,4-dihydro-2(1H)-quinolinone, is a carbostyril compound useful as the effective ingredient for treating schizophrenia (JP-A-2-191256, U.S. Pat. No. 5,006, 528). Aripiprazole is also known as 7-[4-[4-(2,3-dichlorophenyl)-1-piperazinyl]butoxy]-3,4-dihydrocarbostyril, Abilify, OPC-14597, OPC-31 and BMS-337039. Aripiprazole possesses 5-HT1A receptor agonist activity, and is known as a useful compound for treating types of depression and refractory depression, such as endogenous depression, major depression, melancholia and the like (WO 02/060423A2; Jordan et al. U.S. Patent Application 2002/0173513A1). Aripiprazole has activity as an agonist at serotonin receptors and dopamine receptors, and acts as an agonist or partial agonist at the serotonin 5-HT1A receptor and as an agonist or partial agonist at the dopamine $D_2$ receptor.

Aripiprazole is an antipsychotic drug having new mechanism of action which is different from that of other atypical antipsychotic drugs (Grunder, G. et al., Arch Gen Psychiatry, 60(10), pp 974-977, 2003). The available typical and atypical antipsychotic drugs act as antagonists at the dopamine-$D_2$ receptors. In contrast, aripiprazole acts as a partial agonist at the dopamine $D_2$ receptor (By Ishigooka Jyunya and Inada Ken, RINSHO SEISHIN YAKURI, Vol. 4, pp 1653-1664 (2001); Burris, K. D. et al., J. Pharmacol. Exp. Ther., 302, pp 381-389 (2002)). In addition to the partial agonist action at dopamine-$D_2$ receptors, aripiprazole has activity as a partial agonist at the serotonin 5-HT1A receptors, as well as antagonist action at serotonin 5-HT2A receptors. Accordingly, aripiprazole is a drug belonging to new category defined as a dopamine-serotonin system stabilizer (dopamine-serotonin stabilizer (Burris, K. D. et al., J. Pharmacol, Exp. Ther., 302, pp 381-389, 2002; Jordan, S. et al., Eur. J. Pharmacol. 441, pp 137-140, 2002; Grunder, G. et al., Arch Gen Psychiatry, 60(10), pp 974-977, 2003).

Methods of Preparing Aripiprazole

Aripiprazole and aripiprazole metabolites to be used in the present invention may be any of form, for example, free bases, polymorphisms of every type of crystal, hydrate, salts (acid addition salts, etc.) and the like. Among of these forms, Anhydrous Aripiprazole Crystals B is a preferred form.

As to method for preparing the Anhydrous Aripiprazole Crystals B, for example it is prepared by heating aripiprazole hydrate A as follows.

Aripiprazole Hydrate A

The aripiprazole hydrate A having the physicochemical properties shown in (1)-(5) as follows:

(1) It has an endothermic curve which is substantially identical to the thermogravimetric/differential thermal analysis (heating rate 5° C./min) endothermic curve shown in FIG. 1. Specifically, it is characterized by the appearance of a small peak at about 71° C. and a gradual endothermic peak around 60° C. to 120° C.

Figure 2:
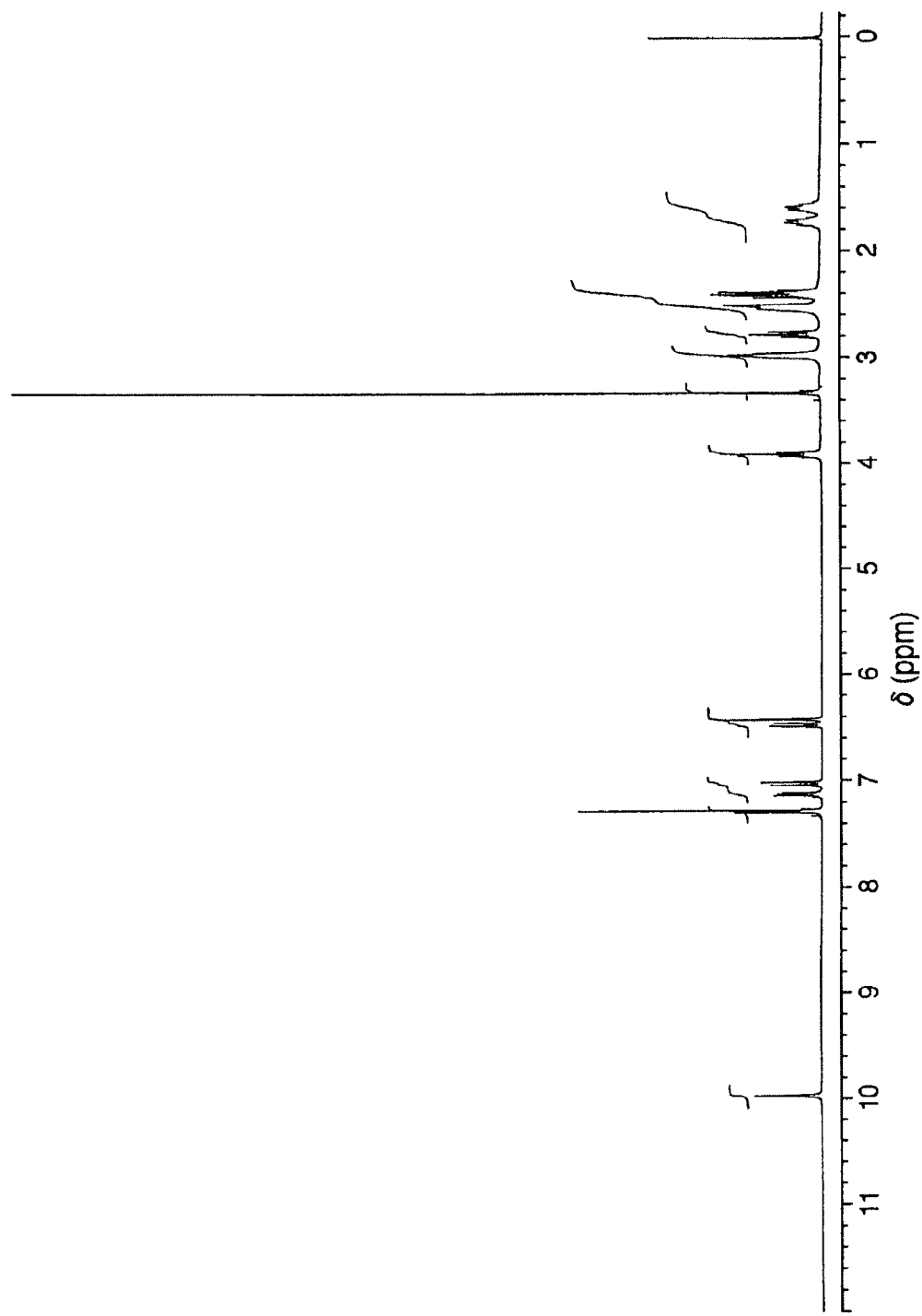
FIG. 2 is the $^1$H-NMR spectrum (DMSO-$d_6$, TMS) of the aripiprazole hydrate A obtained in Reference Example 4.

(2) It has an $^1$H-NMR spectrum which is substantially identical to the $^1$H-NMR spectrum (DMSO-$d_6$, TMS) shown in FIG. 2. Specifically, it has characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H).

Figure 3:
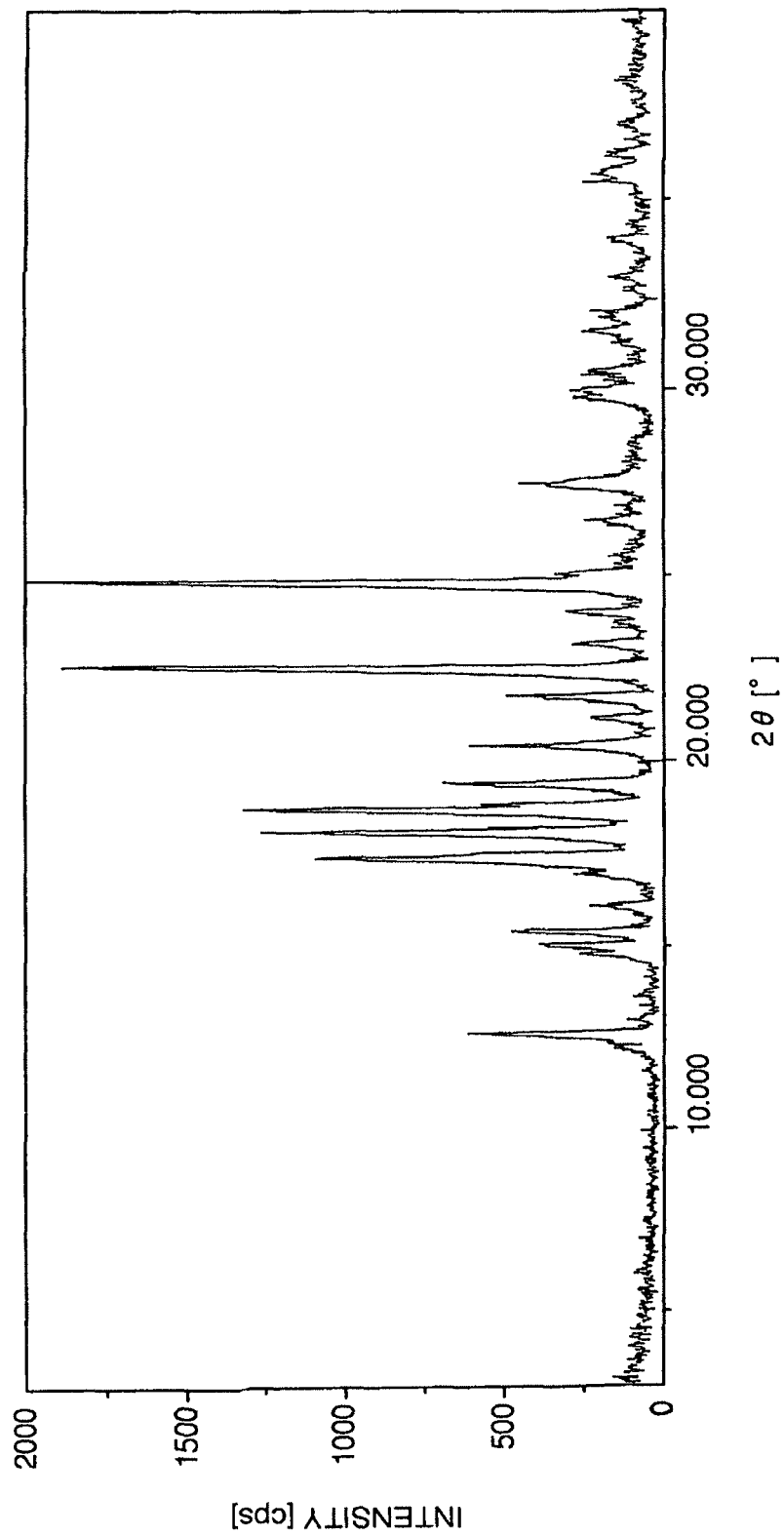
FIG. 3 is the powder X-ray diffraction diagram of the aripiprazole hydrate A obtained in Reference Example 4.

(3) It has a powder x-ray diffraction spectrum which is substantially identical to the powder x-ray diffraction spectrum shown in FIG. 3. Specifically, it has characteristic peaks at 2θ=12.6°, 15.4°, 17.3°, 18.0°, 18.6°, 22.5° and 24.8°.

(4) It has clear infrared absorption bands at 2951, 2822, 1692, 1577, 1447, 1378, 1187, 963 and 784 cm$^{-1}$ on the IR (KBr) spectrum.

(5) It has a mean particle size of 50 μm or less.

Method for Preparing Aripiprazole Hydrate A

Aripiprazole hydrate A is prepared by milling conventional aripiprazole hydrate. Conventional milling methods can be used to mill conventional aripiprazole hydrate. For example, conventional aripiprazole hydrate can be milled in a milling machine. A widely used milling machine such as an atomizer, pin mill, jet mill or ball mill can be used. Among of these, the atomizer is preferably used.

Regarding the specific milling conditions when using an atomizer, a rotational speed of 5000-15000 rpm could be used for the main axis, for example, with a feed rotation of 10-30 rpm and a screen hole size of 1-5 mm.

The mean particle size of the aripiprazole hydrate A obtained by milling may be normally 50 μm or less, preferably 30 μm or less. Mean particle size can be ascertained by the particle size measuring method described hereinafter.

Anhydrous Aripiprazole Crystals B

"Anhydrous Aripiprazole Crystals B" of the present invention have the physicochemical properties given in (6)-(10) below.

Figure 4:
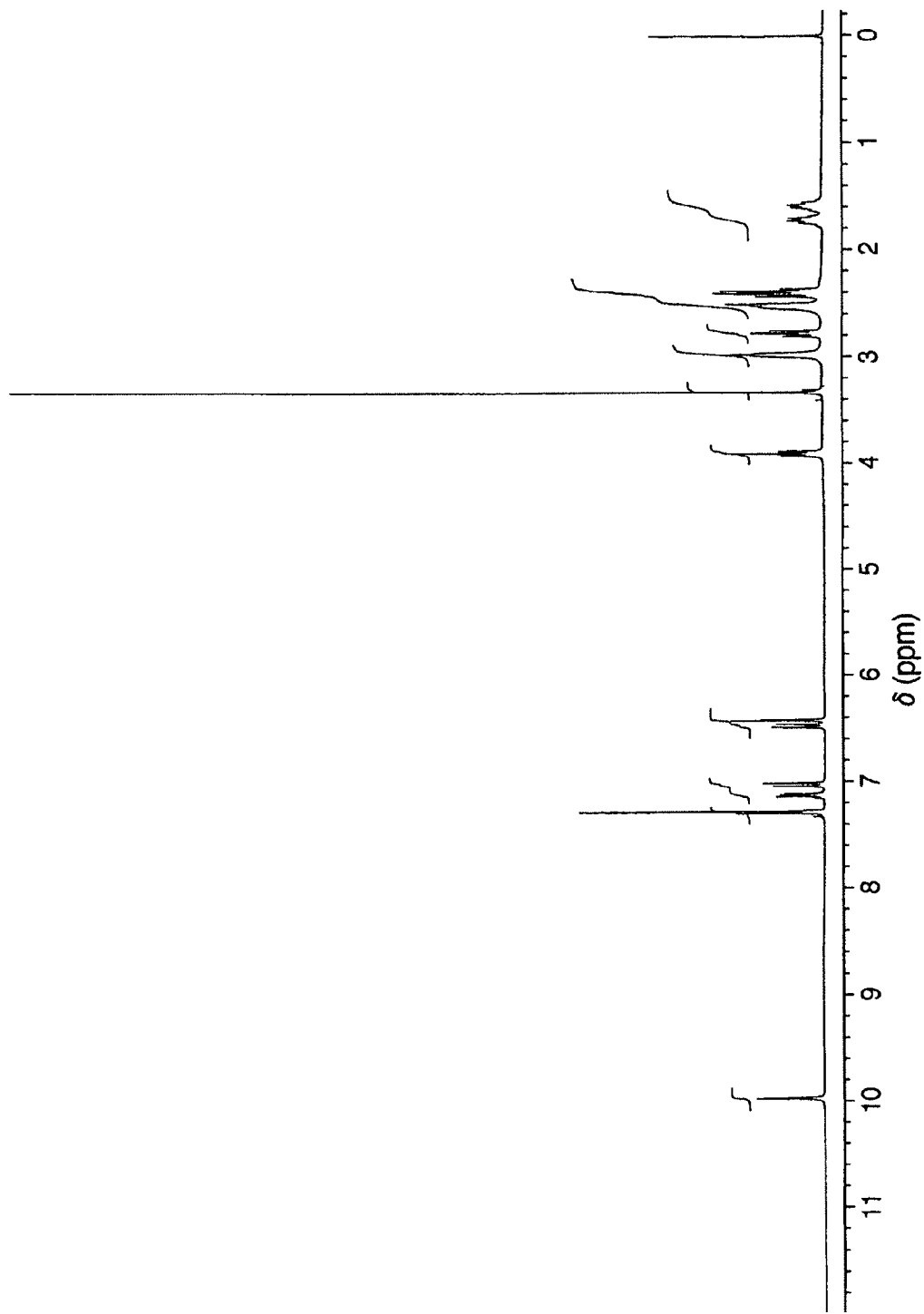
FIG. 4 is the $^1$H-NMR spectrum (DMSO-$d_6$, TMS) of the Anhydrous Aripiprazole Crystals B obtained in Example 1.

(6) They have an $^1$H-NMR spectrum which is substantially identical to the $^1$H-NMR spectrum (DMSO-$d_6$, TMS) shown in FIG. 4. Specifically, they have characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H).

Figure 5:
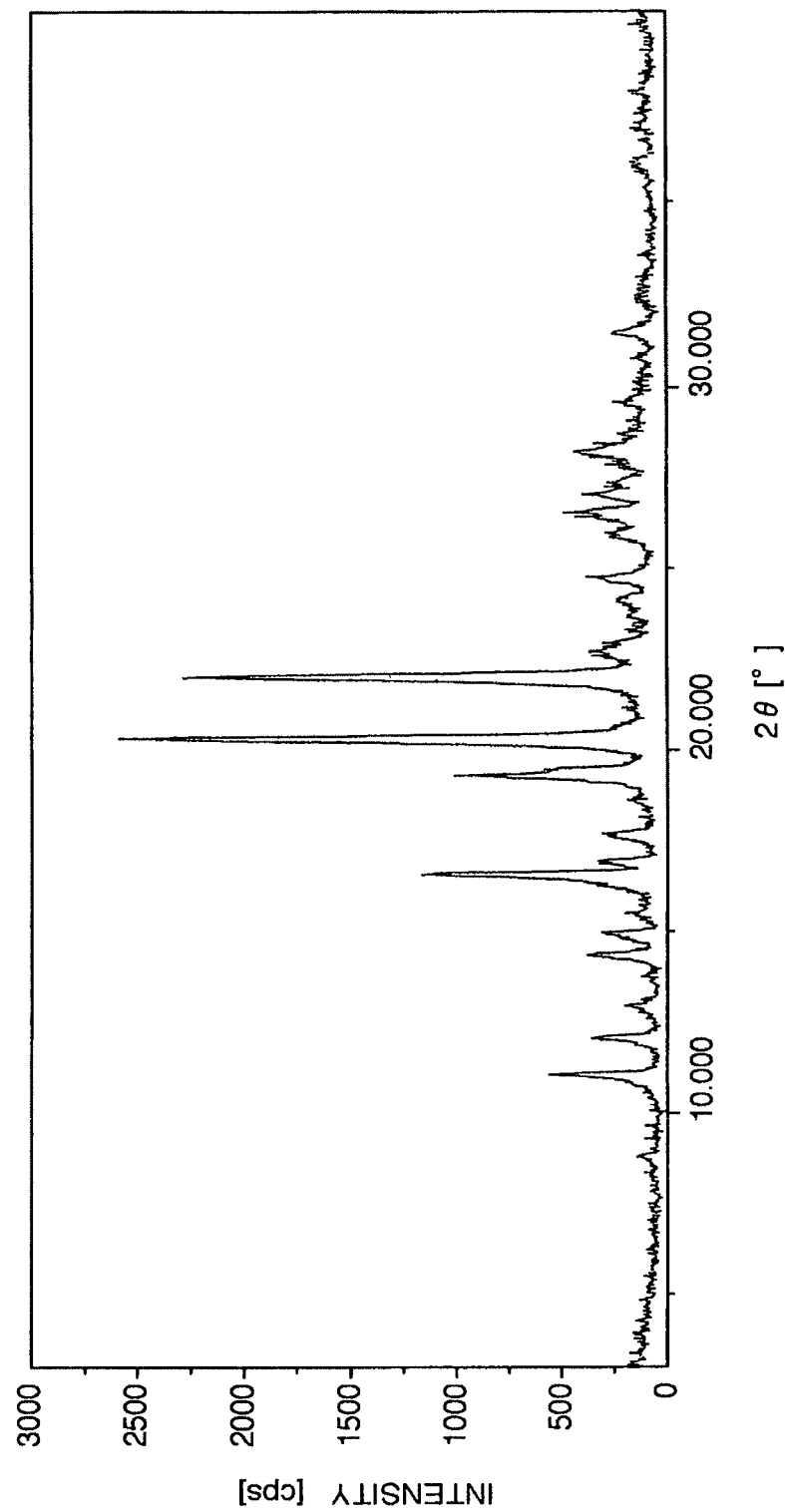
FIG. 5 is the powder X-ray diffraction diagram of the Anhydrous Aripiprazole Crystals B obtained in Example 1.

(7) They have a powder x-ray diffraction spectrum which is substantially identical to the powder x-ray diffraction spectrum shown in FIG. 5. Specifically, they have characteristic peaks at 2θ=11.0°, 16.6°, 19.3°, 20.3° and 22.1°.

(8) They have clear infrared absorption bands at 2945, 2812, 1678, 1627, 1448, 1377, 1173, 960 and 779 cm$^{-1}$ on the IR (KBr) spectrum.

(9) They exhibit an endothermic peak near about 141.5° C. in thermogravimetric/differential thermal analysis (heating rate 5° C./min).

(10) They exhibit an endothermic peak near about 140.7° C. in differential scanning calorimetry (heating rate 5° C./min).

When the small particle size is required for solid preparation, such as tablets and other solid dose formulations including for example flash melt formulations, the mean particle size is preferably 50 μm or less.

Method for preparing Anhydrous Aripiprazole Crystals B

The Anhydrous Aripiprazole Crystals B of the present invention are prepared for example by heating the aforementioned aripiprazole hydrate A at 90-125° C. The heating time is generally about 3-50 hours, but cannot be stated unconditionally, because it differs depending on heating temperature. The heating time and heating temperature are inversely related, so that for example when the heating time is longer, then the heating temperature is lower, and when the heating temperature is higher then the heating time is shorter. Specifically, if the heating temperature of aripiprazole hydrate A is 100° C., the heating time may be 18 hours or more, or preferably about 24 hours. If the heating temperature of aripiprazole hydrate A is 120° C., on the other hand, the heating time may be about 3 hours. The Anhydrous Aripiprazole Crystals B of the present invention can be prepared with certainty by heating aripiprazole hydrate A for about 18 hours at 100° C., and then heating it for about 3 hours at 120° C. The Anhydrous Aripiprazole Crystals B of the present invention can also be obtained if the heating time is extended still further, but this method may not be economical.

When small particle size is not required for the formulation, e.g., when drug substance is being prepared for injectable or oral solution formulations, Anhydrous Aripiprazole Crystals B can be also obtained by the following process.

Anhydrous Aripiprazole Crystals B of the present invention are prepared for example by heating conventional anhydrous aripiprazole crystals at 90-125° C. The heating time is generally about 3-50 hours, but cannot be stated unconditionally because it differs depending on heating temperature. The heating time and heating temperature are inversely related, so that for example if the heating time is longer, the heating temperature is lower, and if the heating time is shorter, the heating temperature is higher. Specifically, if the heating temperature of the anhydrous aripiprazole crystals is 100° C., the heating time may be about 4 hours, and if the heating temperature is 120° C. the heating time may be about 3 hours.

Furthermore, Anhydrous Aripiprazole Crystals B of the present invention are prepared for example, by heating conventional aripiprazole hydrate at 90-125° C. The heating time is generally about 3-50 hours, but cannot be stated unconditionally because it differs depending on heating temperature. The heating time and heating temperature are inversely related, so that for example, if the heating time is longer, the heating temperature is lower, and if the heating time is shorter, the heating temperature is higher. Specifically, if the heating temperature of the aripiprazole hydrate is 100° C., the heating time may be about 24 hours, and if the heating temperature is 120° C. the heating time may be about 3 hours.

The anhydrous aripiprazole crystals which are the raw material for preparing the Anhydrous Aripiprazole Crystals B of the present invention are prepared for example by Method a or b below.

"Method a": Process for Preparing Crude Crystals of Aripiprazole

Conventional anhydrous aripiprazole crystals are prepared by well-known methods, as described in Example 1 of Japanese Unexamined Patent Publication No. 191256/1990.

7-(4-bromobutoxy)-3,4-dihydrocarbostyril, is reacted with 1-(2,3-dichlorophenyl)piperazine and the thus obtained crude aripiprazole crystals are recrystallized from ethanol.

"Method b": Process for Preparing Conventional Anhydrous Aripiprazole

The Method b is described in the Proceedings of the 4th Joint Japanese-Korean Symposium on Separation Technology (Oct. 6-8, 1996).

The aripiprazole hydrate which is the raw material for preparing the Anhydrous Aripiprazole Crystals B of the present invention is prepared for example by Method c below.

"Method c": Method for Preparing Conventional Aripiprazole Hydrate

Aripiprazole hydrate is easily obtained by dissolving the anhydrous aripiprazole crystals obtained by Method a above in a hydrous solvent, and heating and then cooling the resulting solution. Using this method, aripiprazole hydrate is precipitated as crystals in the hydrous solvent.

An organic solvent containing water is usually used as the hydrous solvent. The organic solvent may be preferable one which is miscible with water, for example an alcohol such as methanol, ethanol, propanol or isopropanol, a ketone such as acetone, an ether such as tetrahydrofuran, dimethylformamide, or a mixture thereof, ethanol is particularly desirable. The amount of water in the hydrous solvent may be 10-25% by volume of the solvent, or preferably close to 20% by volume.

Aripiprazole can easily form an acid addition salt with a pharmaceutically acceptable acid. As to such acid, for example, an inorganic acid, such as sulfuric acid, nitric acid, hydrochloric acid, phosphoric acid, hydrobromic acid, etc.; an organic acid such as, acetic acid, p-toluenesulfonic acid, methanesulfonic acid, oxalic acid, maleic acid, fumaric acid, malic acid, tartaric acid, citric acid, benzoic acid, succinic acid, etc. can be exemplified. Similar to aripiprazole of free forms, these acid addition salts can also be used as the active ingredient compounds in the present invention.

The objective compound thus obtained through each one of production steps, is separated from the reaction system by usual separation means, and can be further purified. As to the separation and purification means, for example, distillation method, solvent extraction method, dilution method, recrystallization method, column chromatography, ion-exchange chromatography, gel chromatography, affinity chromatography, preparative thin-layer chromatography and the like can be exemplified.

The Pharmaceutical Composition: The Second Ingredient

In the composition of the present invention, a serotonin reuptake inhibitor is used as the second ingredient. Compounds which function as serotonin reuptake inhibitors can be widely used as the serotonin reuptake inhibitors and are known to one of ordinary skill in the art.

Among the serotonin reuptake inhibitors, those having $IC_{50}$ value (a concentration of the drug that inhibits serotonin reuptake by about 50%), measured by the method of Wong et al. (Neuropsychopharmacology, 8, pp 337-344 (1993)), the standard pharmacological assay method, is about 1000 nM or lower is preferable.

As to such serotonin reuptake inhibitors, for example, fluvoxamine(5-methoxy-1-[4-(trifluoro-methyl)phenyl]-1-pentanone-O-(2-aminoethyl)oxime), fluoxetine (N-methyl-3-(p-trifluoromethylphenoxy)-3-phenylpropylamine), paroxetine (trans-(−)-3-[(1,3-benzodioxol-5-yloxy)methyl]-4-(4-fluorophenyl)-piperidine), sertraline (1S-cis)-4-(3,4-dichlorophenyl)-1,2,3,4-tetrahydro-N-methyl-1-naphthylylamine hydrochloride), venlafaxine, milnacipran (N,N-diethyl-2-aminomethyl-1-phenylcyclopropanecarboxyamide), citalopram, escitalopram, duloxetine and the like may be used.

The serotonin reuptake inhibitor may be either in the form of a free base or a salt (an acid addition salt or the like). Further, the serotonin reuptake inhibitor may be either a racemic modifications or R and S enantiomers.

The serotonin reuptake inhibitors may be either a single use of one serotonin reuptake inhibitor, and in case of need, two or more of the serotonin reuptake inhibitors may be used in combination. Use of one serotonin reuptake inhibitor is preferred.

The serotonin reuptake inhibitor can easily form an acid addition salt with a pharmaceutically acceptable acid. As to such acid, for example, an inorganic acid, such as sulfuric acid, nitric acid, hydrochloric acid, phosphoric acid, hydrobromic acid, etc.; an organic acid such as, acetic acid, p-toluenesulfonic acid, methanesulfonic acid, oxalic acid, maleic acid, fumaric acid, malic acid, tartaric acid, citric acid, benzoic acid, succinic acid, etc. can be exemplified. Similar to the reuptake inhibitor of free forms, these acid addition salts can be also used as the active ingredient compounds in the present invention.

Among the serotonin reuptake inhibitors, a compound having acidic group can easily form salt by reacting with a pharmaceutically acceptable basic compound. As to such basic compound, a metal hydroxide, for example, sodium hydroxide, potassium hydroxide, lithium hydroxide, calcium hydroxide and the like; an alkali metal carbonate or bicarbonate, for example sodium carbonate, potassium carbonate, sodium hydrogencabonate, potassium hydrogencarbonate and the like; a metal alcoholate, for example sodium methylate, potassium ethylate and the like can be exemplified.

The thus obtained salt form of serotonin reuptake inhibitor is separated from the reaction system by usual separation means, and can be further purified. As to the separation and purification means, for example, distillation method, solvent extraction method, dilution method, recrystallization method, column chromatography, ion-exchange chromatography, gel chromatography, affinity chromatography, preparative thin-layer chromatography and the like can be exemplified.

Combination of the First Ingredient with the Second Ingredient

As to combination of carbostyril derivatives with activity as dopamine-serotonin system stabilizers, non-limiting examples of aripiprazole and dehydroaripiprazole are described herein. When aripiprazole is combined with at least one serotonin reuptake inhibitor, the following are non-limiting examples of such combinations: aripiprazole/fluoxetine, aripiprazole/duloxetine, aripiprazole/venlafaxine, aripiprazole/milnacipran, aripiprazole/citalopram, aripiprazole/fluvoxamine, aripiprazole/paroxetine, and aripiprazole/sertraline. A preferred embodiment comprises a combination of aripiprazole/citalopram.

Figure 8:
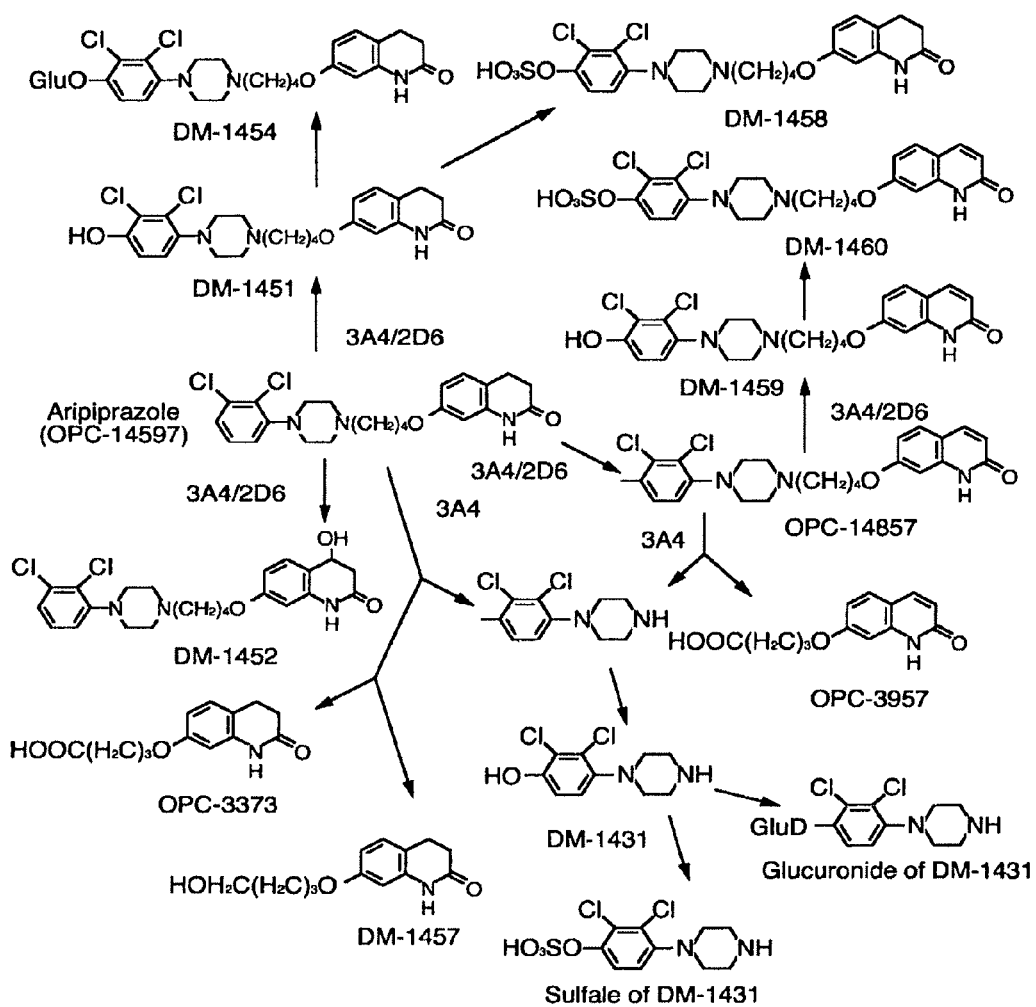
FIG. 8 is a schematic representation of the chemical structures of aripiprazole and metabolites thereof. Some of the metabolites may be formed through other possible pathways; for example, DM-1431 could be formed by N-dealkylation of DM-1451 and DM-1459.

In another embodiment of the present invention, aripiprazole, or a metabolite thereof may be combined with more than one serotonin reuptake inhibitor. Metabolites of aripiprazole that may be used in the present invention include but are not limited to OPC-14857, DM-1458, DM-1451, DM-1452, DM-1454 and DCPP as shown in FIG. 8. Any one of these metabolites may be used in the present invention. The following sentences describe a combination of dehydroaripiprazole with specific serotonin reuptake inhibitors, however it is to be understood that any one of DM-1458, DM-1451, DM-1452, DM-1454 or DCPP, as shown in FIG. 8, could be substituted for dehydroaripiprazole in these disclosed combinations. Dehydroaripiprazole (also called OPC-14857 in FIG. 8) is a preferred metabolite of aripiprazole. As to combination of dehydroaripiprazole with serotonin reuptake inhibitor, the following are non-limiting examples of such combinations: dehydroaripiprazole/fluoxetine, dehydroaripiprazole/duloxetine, dehydroaripiprazole/venlafaxine, dehydroaripiprazole/milnacipran, dehydroaripiprazole/citalopram, dehydroaripiprazole/fluvoxamine, dehydroaripiprazole/paroxetine, and dehydroaripiprazole/sertraline. A preferred embodiment comprises a combination of dehydroaripiprazole and citalopram.

Method of Treating a Mood Disorder, Especially Major Depressive Disorder

Patients with mood disorders may be treated with the compositions of the present invention. A preferred disorder treated with the method and compositions of the present invention is depression or major depressive disorder. Treatment comprises administration of the compositions of the present invention to a patient with a mood disorder such as depression or major depressive disorder, in an amount and dose regimen effective to treat the mood disorder.

Dosage

Dosage of the drug used in the present invention is decided by considering the properties of each constituting drug to be combined, the properties of drugs being after combination and symptoms of the patient (existence of other diseases beside mood disorders such as depression or major depressive disorder). General outlines of the dosage can be applied the following guidelines.

Aripiprazole or a metabolite, such as dehydroaripiprazole, DM-1458, DM-1451, DM-1452, DM-1454 or DCPP: generally about 0.1 to 100 mg/once a day (or about 0.05 to about 50 mg/twice a day), preferably about 1 to 30 mg/once a day (or about 0.5 to about 15 mg/twice a day).

The aripiprazole, or a metabolite thereof, may be combined with at least one of any of the following SRIs at the dosage ranges indicated:

Fluoxetine: generally about 1 to about 80 mg/once a day, preferably about 10 to about 40 mg/once a day;

Duloxetine: generally about 1 to 160 mg/once a day (or 80 mg/twice a day), preferably about 5 to about 20 mg/once a day;

Venlafaxine: generally about 10 to 150 mg/1 to 3 times a day, preferably about 25 to 125 mg/3 times a day;

Milnacipran: generally about 10 to 100 mg/1 to 2 times a day, preferably about 25 to about 50 mg/twice a day;

Citalopram: generally about 5 to about 50 mg/once a day, preferably about 10 to about 30 mg/once a day;

Escitalopram: generally about 5 to about 30 mg/once a day, preferably about 10 to about 20 mg/once a day;

Fluvoxamine: generally about 20 to 500 mg/once a day, preferably about 50 to 300 mg/once a day;

Paroxetine: generally about 20 to about 50 mg/once a day, preferably about 20 to about 30 mg/once a day; or Sertraline: generally, about 20 to about 500 mg/once a day, preferably about 50 to about 200 mg/once a day.

Generally, the weight ratio of the first ingredient to the second ingredient is selected in accordance with the above-mentioned guideline. As to the ratio of the first ingredient and the second ingredient, if the first ingredient is about 1 part by weight of the former, the second ingredient is used about 0.01 to about 500 parts by weight, preferably about 0.1 to about 100 parts by weight.

Pharmaceutically Acceptable Carriers

Pharmaceutically acceptable carriers include diluents and excipients generally used in pharmaceutical preparations, such as fillers, extenders, binders, moisturizers, disintegrators, surfactant, and lubricants.

The pharmaceutical composition of the present invention may be formulated as an ordinary pharmaceutical preparation, for example in the form of tablets, flash melt tablets, pills, powder, liquid, suspension, emulsion, granules, capsules, suppositories or injection (liquid, suspension, etc.), troches, intranasal spray percutaneous patch and the like.

In case of shaping to tablet formulation, a wide variety of carriers that are known in this field can be used. Examples include lactose, saccharose, sodium chloride, glucose, urea, starch, xylitol, mannitol, erythritol, sorbitol, calcium carbonate, kaolin, crystalline cellulose, silic acid and other excipients; water, ethanol, propanol, simple syrup, glucose solution, starch solution, gelatin solution, carboxymethyl cellulose, shellac, methyl cellulose, potassium phosphate, polyvinyl pyrrolidone and other binders; dried starch, sodium alginate, agar powder, laminaran powder, sodium hydrogencarbonate, calcium carbonate, polyoxyethylene sorbitan fatty acid esters, sodium lauryl sulfate, stearic acid monoglyceride, starch, lactose and other disintegrators; white sugar, stearin, cacao butter, hydrogenated oil and other disintegration inhibitors; quaternary ammonium salt, sodium lauryl sulfate and other absorption accelerator; glycerine, starch and other moisture retainers; starch, lactose, kaolin, bentonite, colloidal silic acid and other adsorbents; and refined talc, stearate, boric acid powder, polyethylene glycol and other lubricants and the like. Tablets can also be formulated if necessary as tablets with ordinary coatings, such as sugar-coated tablets, gelatin-coated tablets, enteric coated tablets and film coated tablets, as well as double tablets and multilayered tablets.

In case of shaping to pills, a wide variety of carriers that are known in this field can be used. Examples include glucose, lactose, starch, cacao butter, hardened vegetable oil, kaolin, talc and other excipients; gum arabic powder, traganth powder, gelatin, ethanol and other binders; and laminaran, agar and other disintegrators and the like.

In case of shaping to a suppository formulation, a wide variety of carriers that are known in the field can be used. Examples include polyethylene glycol, cacao butter, higher alcohol, esters of higher alcohol, gelatin semi-synthetic glyceride and the like.

Capsules are prepared according to ordinary methods by mixing carbostyril derivatives such as anhydrous aripiprazole crystals as the first ingredient and serotonin reuptake inhibitor as the second ingredient, and the various carriers described above and packing them in hard gelatin capsules, soft capsules hydroxypropylmethyl cellulose capsules (HPMC capsules) and the like.

In addition, colorants, preservatives, perfumes, flavorings, sweeteners and the like as well as other drugs may be contained in the pharmaceutical composition.

The amounts of the first ingredient and the second ingredient to be contained in the pharmaceutical composition of the present invention are suitably selected from a wide range depending on the diseases to be treated. Generally, about 1 to 70 parts by weight, preferably about 1 to 30 parts by weight of the first ingredient and the second ingredient in the total amount on the basis of the pharmaceutical composition.

The methods for administration of the pharmaceutical composition of the present invention are not specifically restricted. The composition is administered depending on each type of preparation forms, and the age, gender and other condition of the patient (degree and conditions of the disease, etc.). For example, tablets, pills, liquids, suspensions, emulsions, granules and capsules are administered orally. In case of injection preparation, it is administered intravenously by either singly or mixed with a common auxiliary liquid such as solutions of glucose or amino acid. Further, if necessary, the injection preparation is singly administered intracutaneously, subcutaneously or intraperitoneally. In case of a suppository, it is administered intrarectally.

Administration forms of the pharmaceutical composition of the present invention may be any type by which the effective levels of both carbostyril derivatives and serotonin reuptake inhibitors can be provide in vivo at the same time. In one embodiment, a carbostyril derivative together with a serotonin reuptake inhibitor are contained in one pharmaceutical composition and this composition may be administered. On the other hand, each one of carbostyril derivative and a serotonin reuptake inhibitor are contained individually in a pharmaceutical preparation respectively, and each one of these preparations may be administered at the same time or in suitable intervals.

Dosage of the pharmaceutical composition of the present invention for treating and improving depression or major depressive disorder may be used relatively in a small amount, because the composition possesses excellent efficacy. Therefore the composition has fewer side-effects and an excellent safety profile.

The pharmaceutical composition of the present invention is quite effective for treating or improving mood disorders such as depressive symptoms, depression, refractory depression, major depressive disorder and the like.

The pharmaceutical composition of the present invention can be manifest in a wide range of neurotransmission accommodation actions. As a result, the composition of the present invention establishes pseudo-homeostatic dopaminergic and serotoninergic neurotransmission (as a result of partial agonism), which, as a result of neuropathophysiological processes has ceased to function normally.

The mood disorders which can be treated by the pharmaceutical composition of the present invention includes the mood disorders being classified in "Diagnostic and Statistical Manual of Mental Disorders" Fourth Edition (DSM-IV) published by the American Psychiatric Association. These mood disorders include, for example, major depressive disorder, all mood disorders, schizoaffective disorder, dementia with depressive symptoms and the like. A preferred disorder to be treated with the present invention is major depressive disorder.

The pharmaceutical composition of the present invention is useful for treating major depressive disorder, endogenous depression, melancholia, depression in combination with psychotic episodes, bipolar disorder with depressive phase, refractory depression, dementia of the Alzheimer's type with depressive symptoms, Parkinson's disease with depressive symptom, senile dementia, mood disorder associated with cerebral blood vessels and mood disorder following head injury and the like. In addition to the methods for treatment described herein, additional disclosure for designing clinical studies is provided in J. Clin. Psychiatry, 2002, 63:(12), pp 1164-1170; J. Clin. Psychiatry, 2002, 63:(8), pp 733-736; and J. Clin. Psychiatry, 2002, 63:(5), pp 391-395.

EXAMPLES

The present invention will be explained more in detail by illustrating Reference Examples, Example and Formulation Sample Examples. First, analytical methods are explained.

Analytical Methods (1) The $^1$H-NMR spectrum was measured in DMSO-$d_6$ by using TMS as the standard.

(2) Powder X-ray Diffraction

By using RAD-2B diffraction meter manufactured by Rigaku Denki, the powder x-ray diffraction pattern was measured at room temperature by using a Cu Kα filled tube (35 kV 20 mA) as the x-ray source with a wide-angle goniometer, a 1° scattering slit, an 0.15 mm light-intercepting slit, a graphite secondary monochromator and a scintillation counter. Data collection was done in 2θ-continuous scan mode at a scan speed of 5°/minute in scan steps of 0.02° in the range of 3° to 40°.

(3) The IR spectrum was measured by the KBr method.

(4) Thermogravimetric/Differential Thermal Analysis

Thermogravimetric/differential thermal analysis was measured by using SSC 5200 control unit and TG/DTA 220 simultaneous differential thermal/thermogravimetric measuring unit manufactured by Seiko Corp. Samples (5-10 mg) were placed in open aluminum pans and heated at from 20° C. to 200° C. in a dry nitrogen atmosphere at a heating rate of 5° C./minute. α-Alumina was used as the standard substance.

(5) Differential Scanning calorimetry

Thermogravimetric/differential thermal analysis was measured by using SSC 5200 control unit and DSC 220C differential scanning calorimeter manufactured by Seiko Corp. Samples (5-10 mg) were placed in crimped aluminum pans and heated from 20° C. to 200° C. in a dry nitrogen atmosphere at a heating rate of 5° C./minute. α-Alumina was used as the standard substance.

(6) Particle Size Measurement

The particles (0.1 g) to be measured were suspended in a 20 ml n-hexane solution of 0.5 g soy lecithin, and particle size was manufactured by using a size distribution measuring meter (Microtrack HRA, manufactured by Microtrack Co.).

Reference Example 1

7-(4-Cholorobutoxy)-3,4-dihydrocarbostyril (19.4 g) and monohydrochloride 16.2 g of 1-(2,3-dichlorophenyl)piperadine 1 hydrochloride were added to a solution of 8.39 g of potassium carbonate dissolved in 140 ml of water, and refluxed for 3 hours under agitation. After the reaction was complete, the mixture was cooled and the precipitated crystals collected by filtration. These crystals were dissolved in 350 ml of ethyl acetate, and about 210 ml of water/ethyl acetate azeotrope was removed under reflux. The remaining solution was cooled, and the precipitated crystals were collected by filtration. The resulting crystals were dried at 60° C. for 14 hours to obtain 20.4 g (74.2%) of crude product of aripiprazole.

The crude product of aripiprazole (30 g) obtained above was recrystallized from 450 ml of ethanol according to the methods described in Japanese Unexamined Patent Publication No. 191256/1990, and the resulting crystals were dried at 80° C. for 40 hours to obtain anhydrous aripiprazole crystals. The yield was 29.4 g (98.0%).

The melting point (mp) of these anhydrous aripiprazole crystals was 140° C., which is identical to the melting point of the anhydrous aripiprazole crystals described in Japanese Unexamined Patent Publication No. 191256/1990.

Reference Example 2

The crude product of aripiprazole (6930 g) obtained in Reference Example 1 was heat dissolved by heating in 138 liters of hydrous ethanol (water content 20% by volume) according to the method presented at the 4th Joint Japanese-Korean Symposium on Separation Technology, the solution was gradually (2-3 hours) cooled to room temperature, and then was chilled to near 0° C. The precipitated crystals were collected by filtration, about 7200 g of aripiprazole hydrate (wet-state).

The wet-state aripiprazole hydrate crystals obtained above were dried at 80° C. for 30 hours to obtain 6480 g (93.5%) of anhydrous aripiprazole crystals. The melting point (mp) of these crystals was 139.5° C.

Further, the crystalline form of these crystals was colorless flake.

The water content of the crystals were confirmed by the Karl Fischer method, the moisture value was 0.03%, thus the crystals were confirmed as anhydrous product.

Reference Example 3

Figure 6:
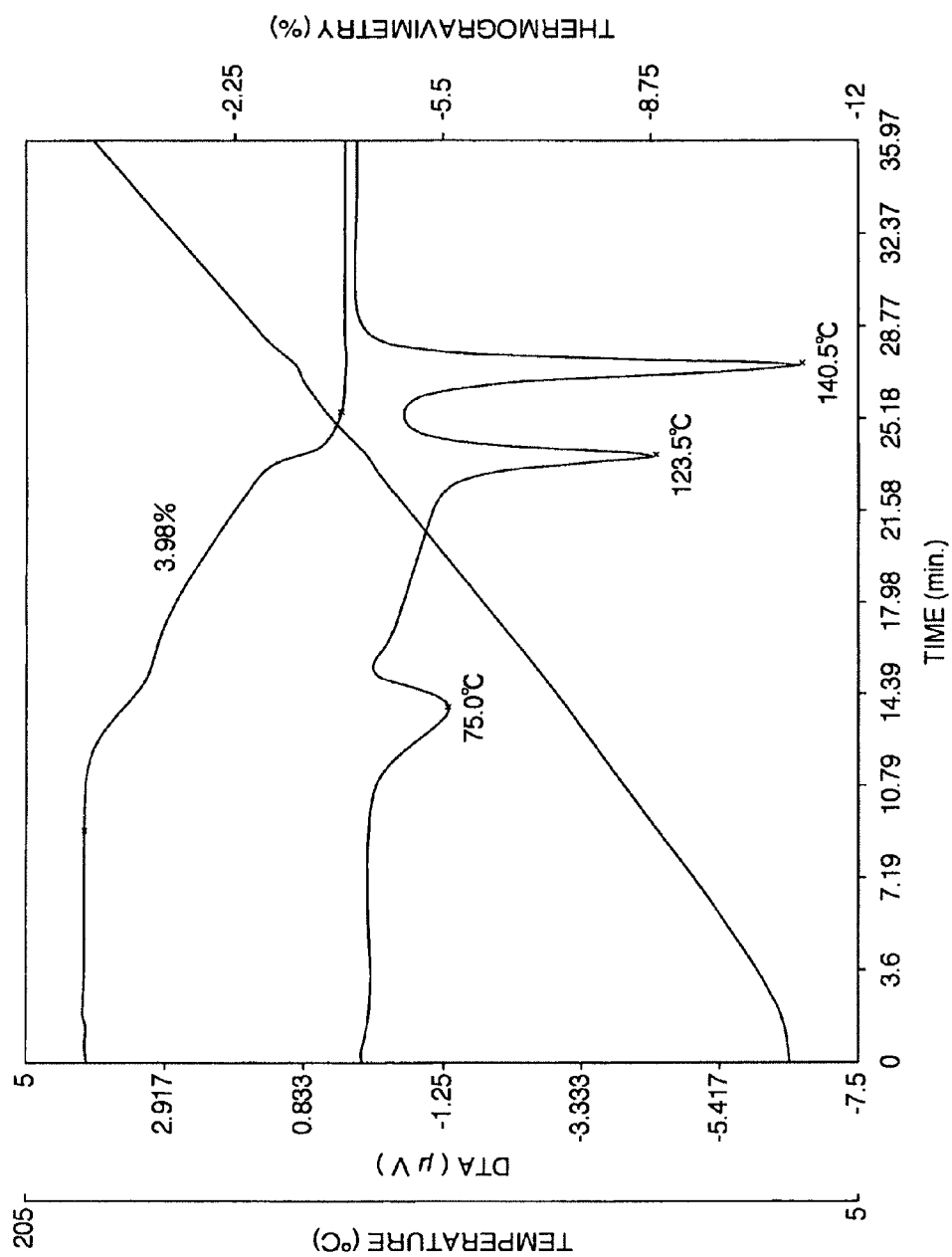
FIG. 6 is the thermogravimetric/differential thermogram of the aripiprazole hydrate A obtained in Reference Example 3.

The aripiprazole hydrate (820 g) in wet state obtained from Reference Example 2 was dried at 50° C. for 2 hours to obtain 780 g of aripiprazole hydrate crystals. The moisture value of the crystals had a moisture value was 3.82% measured according to the Karl Fischer method. As shown in FIG. 6, thermogravimetric/differential thermal analysis revealed endothermic peaks at 75.0, 123.5 and 140.5° C. Because dehydration began near at 70° C., there was no clear melting point (mp) was observed.

Figure 7:
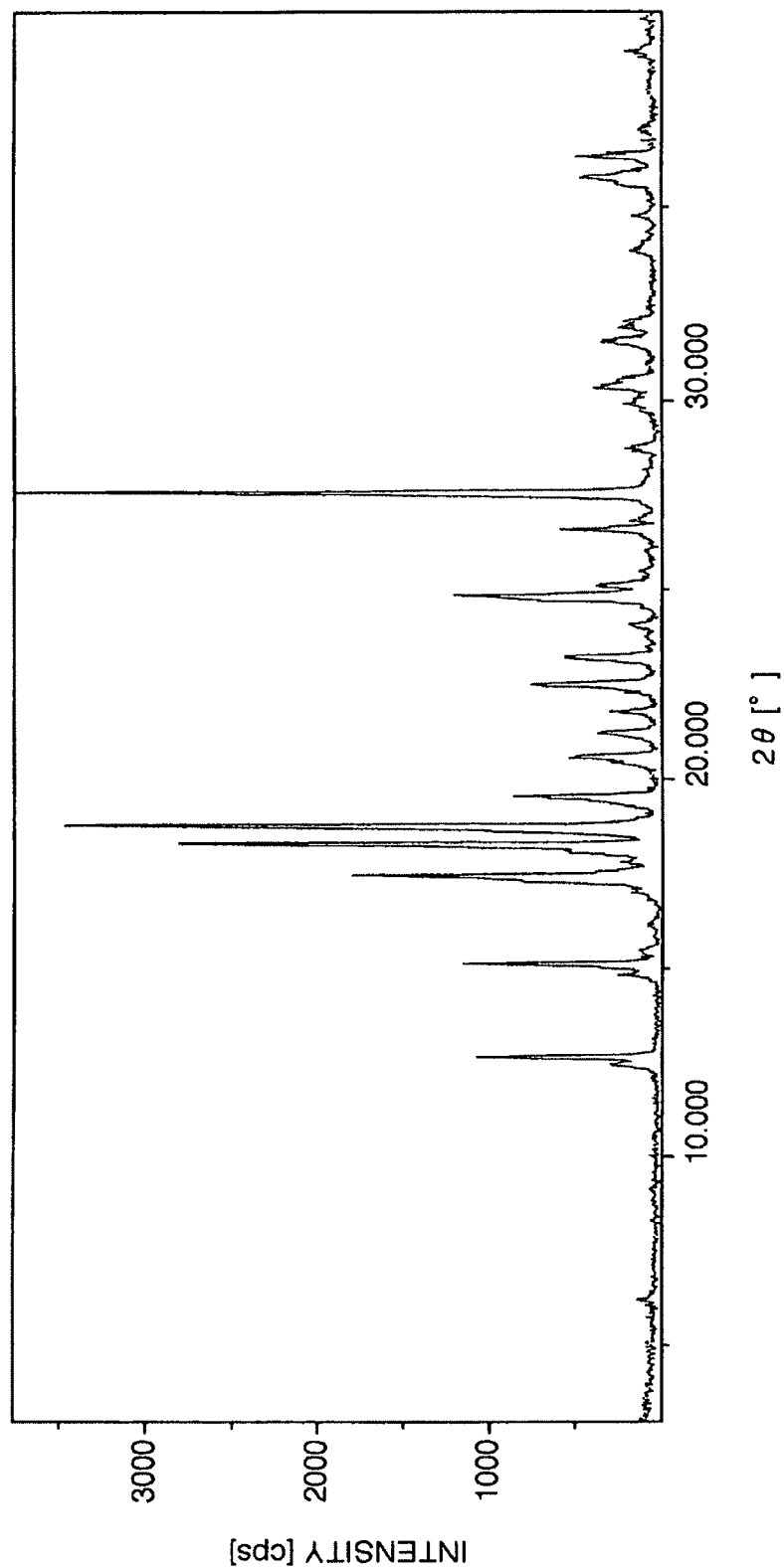
FIG. 7 is the powder X-ray diffraction diagram of aripiprazole hydrate obtained in Reference Example 3.

As shown in FIG. 7, the powder x-ray diffraction spectrum of aripiprazole hydrate obtained by this method exhibited characteristic peaks at 2θ=12.6°, 15.1°, 17.4°, 18.2°, 18.7°, 24.8° and 27.5°.

The powder x-ray diffraction spectrum of this aripiprazole hydrate was identical to the powder x-ray diffraction spectrum of aripiprazole hydrate presented at the 4th Joint Japanese-Korean Symposium on Isolation Technology.

Reference Example 4

The aripiprazole hydrate crystals (500.3 g) obtained in Reference Example 3 were milled by using a sample mill (small size atomizer). The main axis rotation rate was set to 12,000 rpm and the feed rotation rate to 17 rpm, and a 1.0 mm herringbone screen was used. Milling was finished in 3 minutes, and obtained 474.6 g (94.9%) of powder of aripiprazole hydrate A.

The aripiprazole hydrate A (powder) obtained in this way had a mean particle size of 20-25 μm. The melting point (mp) was undetermined because dehydration was observed beginning near at 70° C.

The aripiprazole hydrate A (powder) obtained above exhibited an $^1$H-NMR (DMSO-$d_6$, TMS) spectrum which was substantially identical to the $^1$H-NMR spectrum shown in FIG. 2. Specifically, it had characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H).

The aripiprazole hydrate A (powder) obtained above had a powder x-ray diffraction spectrum which was substantially identical to the powder x-ray diffraction spectrum shown in FIG. 3. Specifically, it had characteristic peaks at 2θ=12.6°, 15.4°, 17.3°, 18.0°, 18.6°, 22.5° and 24.8°. This pattern is different from the powder x-ray spectrum of unmilled aripiprazole hydrate shown in FIG. 7.

The aripiprazole hydrate A (powder) obtained above had infrared absorption bands at 2951, 2822, 1692, 1577, 1447, 1378, 1187, 963 and 784 $cm^{-1}$ on the IR (KBr) spectrum.

As shown in FIG. 1, the aripiprazole hydrate A (powder) obtained above had a weak peak at 71.3° C. in thermogravimetric/differential thermal analysis and a broad endothermic peak (weight loss observed corresponding to one molecule of water) between 60-120° C. which was clearly different from the endothermic curve of unmilled aripiprazole hydrate (see FIG. 6).

It will be appreciated that other embodiments and uses will be apparent to those skilled in the art and that the invention is not limited to these specific illustrative examples.

Example 1

The aripiprazole hydrate A (powder) (44.29 kg) obtained in the Reference Example 4 was dried at 100° C. for 18 hours by using a hot air dryer and further heated at 120° C. for 3 hours, to obtain 42.46 kg (yield; 99.3%) of Anhydrous Aripiprazole Crystals B. These Anhydrous Aripiprazole Crystals B had a melting point (mp) of 139.7° C.

The Anhydrous Aripiprazole Crystals B obtained above had an $^1$H-NMR spectrum (DMSO-$d_6$, TMS) which was substantially identical to the $^1$H-NMR spectrum shown in FIG. 4. Specifically, they had characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H).

The Anhydrous Aripiprazole Crystals B obtained above had a powder x-ray diffraction spectrum which was substantially the identical to the powder x-ray diffraction spectrum shown in FIG. 5. Specifically, they had characteristic peaks at 2θ=11.0°, 16.6°, 19.3°, 20.3° and 22.1°.

The Anhydrous Aripiprazole Crystals B obtained above had remarkable infrared absorption bands at 2945, 2812, 1678, 1627, 1448, 1377, 1173, 960 and 779 $cm^{-1}$ on the IR (KBr) spectrum.

The Anhydrous Aripiprazole Crystals B obtained above exhibited an endothermic peak near about at 141.5° C. in thermogravimetric/differential thermal analysis. The Anhydrous Aripiprazole Crystals B obtained above exhibited an endothermic peak near about at 140.7° C. in differential scanning calorimetry.

Example 2

Receptor Binding at the 5-HT1A Receptor

1. Materials and Methods
   1.1 Test Compound
   7-{4-[4-(2,3-Dichlorophenyl)-1-piperazinyl]-butoxy}-3,4-dihydrocarbostyril (aripiprazole) was used as test compound.
   1.2 Reference Compounds
   Serotonin (5-HT) and WAY-100635 (N-[2-[4-(2-methoxyphenyl)-1-piperazinyl]ethyl]-N-(2-pyridyl)-cyclohexanecarboxamide, a 5-HT1A receptor antagonist, manufactured by RBI (Natick, Mass.) were used as reference compounds.
   1.3 Vehicle
   Dimethyl sulfoxide (DMSO) manufactured by Sigma Chemical Co. (St. Louis, Mo.) was used as vehicle.
   1.4 Preparation of Test and Reference Compounds
   Test compound was dissolved in 100% dimethyl sulfoxide (DMSO) to yield 100 μM stock solutions (final concentration of DMSO in all tubes containing test compound was 1%, v/v). All other reference compounds were prepared by the same method using double-distilled water rather than DMSO.
   1.5 Experimental Procedure for the [$^{35}$S]GTP$_\gamma$S Binding Assay
   Test and reference compounds were studied in triplicate at 10 different concentrations (0.01, 0.1, 1, 5, 10, 50, 100, 1000, 10000 and 50000 nM) for their effects upon basal [$^{35}$S]GTP$_\gamma$S binding to h5-HT1A CHO cell membranes. Reactions were performed in 5 ml glass test tubes containing 8 μl of test/reference drug mixed with 792 μl of buffer (25 mM Tris HCl, 50 mM NaCl, 5 mM $MgCl_2$, 0.1 mM EGTA, pH=7.4) containing GDP (1 μM), [$^{35}$S]GTP$_\gamma$S (0.1 nM) and h5-HT1A CHO cell membranes (10 μg protein/reaction; NEN Life Science Products, Boston, Mass.; catalog # CRM035, lot #501-60024, GenBank # X13556). Reactions proceeded for 60 min at room temperature and were terminated by rapid filtration through Whatman GF/B filter paper, using a Brandel harvester and 4×3 ml ice-cold buffer washes. $^{35}$S radio-activity bound to the filter paper was measured using liquid scintillation counting (1272 Clinigamma, LKB/Wallach).
   1.6 Experimental Procedure to Determine the Binding Affinity of Test Compound (Aripiprazole) at the h5-HT1A Receptor
   Test compound was studied in triplicate at 10 different concentrations (0.01, 0.1, 1, 10, 50, 100, 500, 1000, 5000 and 10000 nM) to determine its displacement of [$^3$H]8-OH-DPAT (1 nM; NEN Life Sciences; catalog # NET 929, lot #3406035, Specific Activity=124.9 Ci/mmol) binding to h5-HT1A receptors in CHO cell membranes (15-20 μg protein; NEN Life Science Products, catalog # CRM035, lot #501-60024). Membranes (396 μl) were incubated in 5 ml glass tubes containing [$^3$H]8-OH-DPAT (396 μl), test compound or vehicle (8 μl) and buffer A (50 mM Tris.HCl, 10 mM $MgSO_4$, 0.5 mM EDTA, 0.1% (w/v) ascorbic acid, pH=7.4). All assays proceeded for 60 min at room temperature and were terminated by rapid filtration through Whatman GF/B filter paper (presoaked in buffer B; 50 mM Tris.HCl, pH=7.4), using a Brandel harvester and 4×1 ml ice-cold washes with buffer B. Non-specific binding was determined in the presence of 10 μM (+)8-OH-DPAT.
   1.7 Parameters Determined
   Serotonin (5-HT) is a full 5-HT1A receptor agonist which stimulates increases in basal [$^{35}$S]GTP$_\gamma$S binding to h5-HT1A receptors in recombinant CHO cell membranes. The test compound was studied at 10 concentrations to determine effects upon basal [$^{35}$S]GTP$_\gamma$S binding relative to that produced by 10 μM 5-HT. The relative potency ($EC_{50}$, 95% confidence interval) and intrinsic agonist activity (% of $E_{max}$ for 10 μM 5-HT) was calculated for each compound by computerized non-linear regression analysis of complete concentration-effect data. The binding affinity of test compound at the h5-HT1A receptor was determined by its ability to prevent [$^3$H]8-OH-DPAT binding to CHO cell membranes that express this receptor. Non-linear regression analysis of the competition binding data was used to calculate an inhibition constant ($IC_{50}$, 95% confidence interval), which is the concentration of test compound that occupies half of the h5-HT1A sites specifically bound by [$^3$H]8-OH-DPAT. The affinity of h5-HT1A receptors for test compound (Ki, 95% confidence interval) was calculated by the equation, Ki=$(IC_{50})/(1+([[^3H]8\text{-}OH\text{-}DPAT]/Kd)$, where the Kd for [$^3$H]8-OH-DPAT at h5-HT1A=0.69 nM (NEN Life Sciences). All estimates of drug binding affinity, potency and intrinsic efficacy at the h5-HT1A receptor were calculated using GraphPad Prism version 3.00 for Windows (GraphPad Software, San Diego, Calif.).

2. Results

The test compound and 5-HT produced concentration-dependent increases above basal [$^{35}$S]GTP$_\gamma$S binding. 1% DMSO tested alone had no effect upon basal or drug-induced [$^{35}$S]GTP$_\gamma$S binding.

The test compound ($EC_{50}$=2.12 nM), 5-HT ($EC_{50}$=3.67 nM), potently stimulated basal [$^{35}$S]GTP$_\gamma$S binding. Potency and intrinsic agonist efficacy estimates were derived by non-linear regression analysis with correlation coefficients ($r^2$)>0.98 in each case (Table 1). The test compound exerted partial agonist efficacies in the 65-70% range. WAY-100635 produced no significant change (unpaired Student's t-test) in basal [$^{35}$S]GTP$_\gamma$S binding at all concentrations tested (Table 1). WAY-100635 did, however, completely inhibit the effects of 5-HT and test compound upon [$^{35}$S]GTP$_\gamma$S binding to h5-HT1A receptors in CHO cell membranes (Table 2). Tables 1 and 2 are shown below.

The test compound demonstrated high affinity binding to h5-HT1A receptors in CHO cell membranes ($IC_{50}$=4.03 nM, 95% confidence interval=2.67 to 6.08 nM; Ki=1.65 nM, 95% confidence interval=1.09 to 2.48 nM).

TABLE 1

Potency ($EC_{50}$) and Intrinsic Agonist Efficacy ($E_{max}$) of Test compound and Reference Drugs in a h5-HT1A [$^{35}$S] GTP$_\gamma$S CHO-cell Membrane Binding Assay.

| Drug | $EC_{50}$, nM (95% Confidence Interval) | $E_{max}$ (% ± SEM) | Goodness of Fit ($r^2$) |
|---|---|---|---|
| Test Compound | 2.12 (0.87 to 5.16) | 68.13 ± 3.16 | 0.986 |
| 5-HT | 3.67 (1.56 to 8.63) | 98.35 ± 4.47 | 0.986 |
| WAY-100635 | — | — | — |

TABLE 2

Inhibitory Potency ($IC_{50}$) of WAY-100635 versus 1 μM Concentration of 5-HT and Test compound in a h5-HT1A [$^{35}$S] GTP$_\gamma$S CHO-cell Membrane Binding Assay.

| Drug Combination | WAY-100635 Inhibition Potency, $IC_{50}$, nM (95% Confidence Interval) | Goodness of Fit ($r^2$) |
|---|---|---|
| 5-HT + WAY-100635 | 217.1 (127.4 to 369.7) | 0.988 |
| Test compound + WAY-100635 | 392.2 (224.1 to 686.2) | 0.989 |

Example 3

Pharmacological Test

The forced swimming test proposed by Porsolt et al. (Porsolt, R. D. et al.: Arch. Int. Pharmacodyn., 229, 327-336, 1977) is widely used as to an experimental animal model for predicting the antidepressant activity in clinical settings. In this experimental model, a test mouse is put in a cylinder in which a suitable amount of water is contained, and the antidepressant action of a test drug is detected by measuring the immobility time, as the indication, shown by the mouse. It was reported that the action of shortening the immobility time is correlated with clinically observed antidepressive action (Willner, P.: Psychopharmacology, 83: 1-16, 1984). The crisis of depression is closely concerned with lowering of serotonin 5-HT1A receptor neurotransmission action, and the present inventors have found the facts that antidepressive action of antidepressants which affect to serotonin system can be detected more precisely using prolongation of the immobility time performed with WAY-100635, which is a selective serotonin 5-HT1A receptor antagonist. The prolongation of the immobility time performed by WAY-100635 is defined as the indication. In this manner, the antidepressive action of test antidepressants was determined by taking the prolongation of immobility time performed by WAY-100635 in the forced swimming test as the indication.

In a cylinder (diameter: 9 cm, height 20 cm), water was poured therein up to the height of 9.5 cm, from the bottom, then a mouse of ICR strain is placed in the cylinder. After placing the mouse in the cylinder, an immobility time of 6 minutes is measured. During the test, the water temperature is maintained at 23 to 24° C. A test drug is orally administered to the mouse at 1 or 2 hours before placing the mouse in the water. WAY-100635 is administered subcutaneously to the mouse 30 minutes before placing the mouse in the water.

During this test, aripiprazole is used in combination together with citalopram, escitalopram, fluoxetine, venlafaxine or milnacipran. Following such combination administration, a decrease in the immobility time (the antidepressant activity) is observed in comparison with the case of single use of each one of aripiprazole, citalopram, escitalopram, fluoxetine, venlafaxine or milnacipran, respectively.

Further, when aripiprazole is used in combination with citalopram, escitalopram, fluoxetine, venlafaxine or milnacipran, a decrease in the immobility time (the antidepressant activity) is observed in comparison to administration of the available atypical antipsychotic drugs such as olanzapine, quetiapine, risperidone in combination with citalopram, fluoxetine, venlafaxine or milnacipran.

Example 4

Formulation Examples

Several non-limiting formulation examples of aripiprazole, dehydroaripiprazole and other metabolites with serotonin reuptake inhibitors are presented below.

Formulation Sample Example 1

| | |
|---|---|
| Anhydrous Aripiprazole Crystals B | 5 mg |
| Fluoxetine | 20 mg |
| Starch | 131 mg |
| Magnesium stearate | 4 mg |
| Lactose | 60 mg |
| Total | 220 mg |

According to a preparation method which is well-known to a person having an ordinary skill in the art, the tablet containing the above mentioned formulation was prepared.

Formulation Sample Example 2

| | |
|---|---|
| Anhydrous Aripiprazole Crystals B | 5 mg |
| Duloxetine | 20 mg |

| | |
|---|---|
| Starch | 131 mg |
| Magnesium stearate | 4 mg |
| Lactose | 60 mg |
| Total | 220 mg |

According to a common method, the tablet containing the above mentioned formulation was prepared.

Formulation Sample Example 3

| | |
|---|---|
| Anhydrous Aripiprazole Crystals B | 5 mg |
| Venlafaxine | 75 mg |
| Starch | 131 mg |
| Magnesium stearate | 4 mg |
| Lactose | 60 mg |
| Total | 275 mg |

According to a common method, the tablet containing the above mentioned formulation was prepared.

Formulation Sample Example 4

| | |
|---|---|
| Anhydrous Aripiprazole Crystals B | 5 mg |
| Milnacipran | 50 mg |
| Starch | 131 mg |
| Magnesium stearate | 4 mg |
| Lactose | 60 mg |
| Total | 250 mg |

According to a common method, the tablet containing the above mentioned formulation was prepared.

Formulation Sample Example 5

| | |
|---|---|
| Anhydrous Aripiprazole Crystals B | 5 mg |
| Citalopram | 20 mg |
| Starch | 131 mg |
| Magnesium stearate | 4 mg |
| Lactose | 60 mg |
| Total | 220 mg |

According to a common method, the tablet containing the above mentioned formulation was prepared.

Formulation Sample Example 6

| | |
|---|---|
| Anhydrous Aripiprazole Crystals B | 5 mg |
| Fluvoxamine | 50 mg |
| Starch | 131 mg |
| Magnesium stearate | 4 mg |
| Lactose | 60 mg |
| Total | 250 mg |

According to a common method, the tablet containing the above mentioned formulation was prepared.

Formulation Sample Example 7

| | |
|---|---|
| Anhydrous Aripiprazole Crystals B | 5 mg |
| Paroxetine | 20 mg |
| Starch | 131 mg |
| Magnesium stearate | 4 mg |
| Lactose | 60 mg |
| Total | 220 mg |

According to a common method, the tablet containing the above mentioned formulation was prepared.

Formulation Sample Example 8

| | |
|---|---|
| Anhydrous Aripiprazole Crystals B | 5 mg |
| Sertraline | 50 mg |
| Starch | 131 mg |
| Magnesium stearate | 4 mg |
| Lactose | 60 mg |
| Total | 250 mg |

According to a common method, the tablet containing the above mentioned formulation was prepared.

Formulation Sample Example 9

| | |
|---|---|
| Anhydrous Aripiprazole Crystals B | 5 mg |
| Escitalopram | 10 mg |
| Starch | 131 mg |
| Magnesium stearate | 4 mg |
| Lactose | 60 mg |
| Total | 210 mg |

According to a common method, the tablet containing the above mentioned formulation was prepared.

Several non-limiting formulation examples of dehydroaripiprazole and serotonin reuptake inhibitors are presented below. It is to be understood that any one of DM-1458, DM-1451, DM-1452, DM-1454 or DCPP, as shown in FIG. 8, could be substituted for dehydroaripiprazole in these disclosed formulations.

Formulation Sample Example 10

| | |
|---|---|
| Dehydroaripiprazole | 5 mg |
| Fluoxetine | 20 mg |
| Starch | 131 mg |
| Magnesium stearate | 4 mg |
| Lactose | 60 mg |
| Total | 220 mg |

According to a preparation method which is well-known to a person having an ordinary skill in the art, the tablet containing the above mentioned formulation was prepared.

Formulation Sample Example 11

| | |
|---|---:|
| Dehydroaripiprazole | 5 mg |
| Duloxetine | 20 mg |
| Starch | 131 mg |
| Magnesium stearate | 4 mg |
| Lactose | 60 mg |
| Total | 220 mg |

According to a common method, the tablet containing the above mentioned formulation was prepared.

Formulation Sample Example 12

| | |
|---|---:|
| Dehydroaripiprazole | 5 mg |
| Venlafaxine | 75 mg |
| Starch | 131 mg |
| Magnesium stearate | 4 mg |
| Lactose | 60 mg |
| Total | 275 mg |

According to a common method, the tablet containing the above mentioned formulation was prepared.

Formulation Sample Example 13

| | |
|---|---:|
| Dehydroaripiprazole | 5 mg |
| Milnacipran | 50 mg |
| Starch | 131 mg |
| Magnesium stearate | 4 mg |
| Lactose | 60 mg |
| Total | 250 mg |

According to a common method, the tablet containing the above mentioned formulation was prepared.

Formulation Sample Example 14

| | |
|---|---:|
| Dehydroaripiprazole | 5 mg |
| Citalopram | 20 mg |
| Starch | 131 mg |
| Magnesium stearate | 4 mg |
| Lactose | 60 mg |
| Total | 220 mg |

According to a common method, the tablet containing the above mentioned formulation was prepared.

Formulation Sample Example 15

| | |
|---|---:|
| Dehydroaripiprazole | 5 mg |
| Fluvoxamine | 50 mg |
| Starch | 131 mg |
| Magnesium stearate | 4 mg |
| Lactose | 60 mg |
| Total | 250 mg |

According to a common method, the tablet containing the above mentioned formulation was prepared.

Formulation Sample Example 16

| | |
|---|---:|
| Dehydroaripiprazole | 5 mg |
| Paroxetine | 20 mg |
| Starch | 131 mg |
| Magnesium stearate | 4 mg |
| Lactose | 60 mg |
| Total | 220 mg |

According to a common method, the tablet containing the above mentioned formulation was prepared.

Formulation Sample Example 17

| | |
|---|---:|
| Dehydroaripiprazole | 5 mg |
| Sertraline | 50 mg |
| Starch | 131 mg |
| Magnesium stearate | 4 mg |
| Lactose | 60 mg |
| Total | 250 mg |

According to a common method, the tablet containing the above mentioned formulation was prepared.

Formulation Sample Example 18

| | |
|---|---:|
| Dehydroaripiprazole | 5 mg |
| Escitalopram | 10 mg |
| Starch | 131 mg |
| Magnesium stearate | 4 mg |
| Lactose | 60 mg |
| Total | 210 mg |

According to a common method, the tablet containing the above mentioned formulation was prepared.

Example 5

Method of Treatment of Patients Diagnosed with Major Depressive Disorder Who were Previously Non-Responsive or Partially Responsive to Anti-Depressant Medication Aripiprazole is evaluated as an augmentation therapy in depressed patients with major depressive disorder who were previously non-responsive or partially responsive to anti-depressant medication comprising serotonin reuptake inhibitors. These patients currently receive therapy through administration of serotonin reuptake inhibitors.

Patients ranging in age from 18 to 65 years who have been diagnosed with major depressive disorder and are receiving therapy with a serotonin reuptake inhibitor are evaluated to ensure that they have a baseline Hamilton score for depression (item 17) of 14 or higher. Only patients with such Hamilton scores receive treatment. These patients are interviewed to obtain a complete medical and psychiatric history. Aripiprazole is first administered at a dose of 10 mg/day and increased to 30 mg/day as needed in the opinion of the monitoring psychiatrist. Aripiprazole is administered to these patients at a dose of from 10 mg/day to 30 mg/day for a period of at least four weeks, and up to eight weeks for patients who respond well to this treatment during the first four weeks.

An improvement in alleviation of symptoms of depression is observed in these patients following administration of aripiprazole as shown by results of testing performed during and after the duration of aripiprazole administration. The Hamilton test for depression and other measures such as clinical global impression (CGI), abnormal involuntary movement scale (AIMS), Simpson Angus scale (SAS), and Barnes akathesia scale (Barnes), commonly known to one of ordinary skill in the art, are administered to these patients.

Example 6

Method of Treatment of Patients with a New Diagnosis of Major Depressive Disorder A combination of aripiprazole and at least one serotonin reuptake inhibitor is evaluated as a therapy for depression in patients newly diagnosed with major depressive disorder. Patients ranging in age from 18 to 65 years who are diagnosed with major depressive disorder are evaluated to ensure that they have a baseline Hamilton score for depression (item 17) of 14 or higher. Only patients with this Hamilton score receive treatment. These patients are interviewed to obtain a complete medical and psychiatric history. Aripiprazole is first administered at a dose of 10 mg/day and increased to 30 mg/day as needed in the opinion of the monitoring psychiatrist. Aripiprazole is administered to these patients at a dose of from 10 mg/day to 30 mg/day for a period of at least four weeks, and up to eight weeks for patients who respond well to this treatment during the first four weeks. The aripiprazole is administered together with at least one serotonin reuptake inhibitor, wherein the serotonin reuptake inhibitor is fluoxetine, duloxetine, venlafaxine, milnacipran, citalopram, fluvoxamine, paroxetine or sertraline. The dosages to be used for these serotonin reuptake inhibitors are provided elsewhere in this patent application.

The aripiprazole can be administered in one dosage form, for example a tablet, and the serotonin reuptake inhibitor may be administered in a separate one dosage form, for example a tablet. The administration may occur at about the same time or at different times during the day.

Alternatively, a dosage form containing aripiprazole in combination with at least one serotonin reuptake inhibitor may be administered. Such combinations include without limitation the following: aripiprazole/fluoxetine, aripiprazole/duloxetine, aripiprazole/venlafaxine, aripiprazole/milnacipran, aripiprazole/citalopram, aripiprazole/fluvoxamine, aripiprazole/paroxetine, and aripiprazole/sertraline. A preferred embodiment comprises a combination of aripiprazole and citalopram.

An improvement in alleviation of symptoms of depression is observed in these patients following administration of aripiprazole and the one or more serotonin reuptake inhibitors as shown by results of testing performed during and after the duration of aripiprazole and serotonin reuptake inhibitor administration. The Hamilton test for depression and other measures such as CGI, AIMS, SAS, Simpson & Angus and Barnes, commonly known to one of ordinary skill in the art, are administered to these patients. Results demonstrate an alleviation of the symptoms of depression.

Example 7

Method of Treatment of Patients Diagnosed with Major Depressive Disorder Who were Previously Non-Responsive or Partially Responsive to Anti-Depressant Medication Dehydroaripiprazole, an active metabolite of aripiprazole, is evaluated as an augmentation therapy in depressed patients with major depressive disorder who were previously non-responsive or partially responsive to anti-depressant medication comprising serotonin reuptake inhibitors. These patients currently receive therapy through administration of serotonin reuptake inhibitors.

Patients ranging in age from 18 to 65 years who have been diagnosed with major depressive disorder and are receiving therapy with a serotonin reuptake inhibitor are evaluated to ensure that they have a baseline Hamilton score for depression (item 17) of 14 or higher. Only patients with such Hamilton scores receive treatment. These patients are interviewed to obtain a complete medical and psychiatric history. Dehydroaripiprazole is first administered at a dose of 10 mg/day and increased to 30 mg/day as needed in the opinion of the monitoring psychiatrist. Dehydroaripiprazole is administered to these patients at a dose of from 10 mg/day to 30 mg/day for a period of at least four weeks, and up to eight weeks for patients who respond well to this treatment during the first four weeks.

An improvement in alleviation of symptoms of depression is observed in these patients following administration of aripiprazole as shown by results of testing performed during and after the duration of aripiprazole administration. The Hamilton test for depression and other measures such as clinical global impression (CGI), abnormal involuntary movement scale (AIMS), Simpson Angus scale (SAS), and Barnes akathesia rating scale (BARS), commonly known to one of ordinary skill in the art, are administered to these patients.

Example 8

Method of Treatment of Patients with a New Diagnosis of Major Depressive Disorder A combination of dehydroaripiprazole and at least one serotonin reuptake inhibitor is evaluated as a therapy for depression in patients newly diagnosed with major depressive disorder. Patients ranging in age from 18 to 65 years who are diagnosed with major depressive disorder are evaluated to ensure that they have a baseline Hamilton score for depression (item 17) of 14 or higher. Only patients with this Hamilton score receive treatment. These patients are interviewed to obtain a complete medical and psychiatric history. Dehydroaripiprazole is first administered at a dose of 10 mg/day and increased to 30 mg/day as needed in the opinion of the monitoring psychiatrist. Dehydroaripiprazole is administered to these patients at a dose of from 10 mg/day to 30 mg/day for a period of at least four weeks, and up to eight weeks for patients who respond well to this treatment during the first four weeks. The dehydroaripiprazole is administered together with at least one serotonin reuptake inhibitor, wherein the serotonin reuptake inhibitor is fluoxetine, duloxetine, venlafaxine, milnacipran, citalopram, fluvoxamine, paroxetine or sertraline.

The dehydroaripiprazole can be administered in one dosage form, for example a tablet, and the serotonin reuptake inhibitor may be administered in a separate one dosage form, for example a tablet. The administration may occur at about the same time or at different times during the day.

Alternatively, a dosage form containing dehydroaripiprazole in combination with at least one serotonin reuptake inhibitor may be administered. Such combinations include without limitation the following: dehydroaripiprazole/fluoxetine, dehydroaripiprazole/duloxetine, dehydroaripiprazole/venlafaxine, dehydroaripiprazole/milnacipran, dehydroaripiprazole/citalopram, dehydroaripiprazole/fluvoxamine, dehydroaripiprazole/paroxetine, and dehydroaripiprazole/sertraline. A preferred embodiment comprises a combination of dehydroaripiprazole and citalopram.

An improvement in alleviation of symptoms of depression is observed in these patients following administration of dehydroaripiprazole and the one or more serotonin reuptake inhibitors as shown by results of testing performed during and after the duration of dehydroaripiprazole and serotonin reuptake inhibitor administration. The Hamilton test for depression and other measures such as CGI, AIMS, SAS, Simpson & Angus and Barnes, commonly known to one of ordinary skill in the art, are administered to these patients. Results demonstrate an alleviation of the symptoms of depression.

All patents, patent applications, scientific and medical publications mentioned herein are hereby incorporated in their entirety. It should be understood, of course, that the foregoing relates only to preferred embodiments of the present invention and that numerous modifications or alterations may be made therein without departing from the spirit and the scope of the invention as set forth in the appended claims.

Example 9

Pharmacological Test

The tail suspension test (TST) was originally described by Steru et al. (1985).[1] A mouse suspended by its tail shows periods of agitation and immobility. The antidepressant activity of a test drug can be detected as an index of shortening the immobility time. This test is widely used as to an experimental animal model for predicting the antidepressant activity of a test drug in clinical settings. An automated device for performing the TST was developed by the authors of the TST (1989).[2] We improved this device and developed our own device incorporating an electric balance, an A/D converter, a testing box (30×25×25 cm), and a personal computer. The mouse was suspended from a hook hanging from the ceiling in the testing box by adhesive tape applied 20 mm from the tip of the tail. The duration of immobility was measured by the computer for a period of 15 min following the start of suspension. The immobility time for a period of 10 min (5-15 min) was evaluated. The experiments were carried out in a sound-proof room.

Aripiprazole was suspended in 0.5% gum arabic-0.9% saline solution and citalopram was dissolved in 0.9% saline solution. Aripiprazole (3 mg/kg) and citalopram (3 mg/kg) were orally administered to mice 60 min before the start of suspension. In this test, the decrease in the immobility time of the combination of aripiprazole with citalopram was statistically significant synergistic effect in comparison with the effects of aripiprazole- and citaroplam-treated groups (Table 3).

REFERENCES

1) Steru L. et al.: The tail suspension test: A new method for screening antidepressants in mice. Psychopharmacology 85, 367(1985).
2) Steru L. and Porsolt R. D.: The automated tail suspension test: A computerized device for evaluating psychotropic activity profiles. Jpn J Clin Pharmacol Ther 20, 77(1989).

TABLE 3

Effects of aripiprazole and citalopram on duration of immobility in the tail suspension test in mice

| Drug | Dose (mg/kg, p.o.) | Immobility time (sec, mean ± SE) | % of shortening for immobility time |
|---|---|---|---|
| Vehicle | — | 499.2 ± 13.6 | — |
| Aripiprazole (Aripi.) | 3 | 486.4 ± 12.3 | 3 |
| Citalopram (Citalo.) | 3 | 468.7 ± 24.2 | 6 |
| Aripi. + Citalo | 3 + 3 | 380.6 ± 19.2**##$ | 24 |

N = 7-9, **p < 0.01 vs. vehicle group (two-tailed t-test),
p < 0.01 vs. aripiprazole alone (two-tailed t-test),
$p < 0.05 vs. citalopram alone (two-tailed t-test).
The decrease in the immobility time of the combination of aripiprazole with citalopram was a statistically significant synergistic effect in comparison with the effects of aripiprazole- and citaroplam-treated groups (p < 0.05, one-way ANOVA).

The invention claimed is:

1. A pharmaceutical composition comprising:
   (a) a compound selected from aripiprazole or a metabolite of aripiprazole, wherein the metabolite of aripiprazole is selected from the group consisting of dehydroaripiprazole, DM-1451 and DM-1452 in combination with
   (b) at least one serotonin reuptake inhibitor selected from the group consisting of fluoxetine, duloxetine, venlafaxine, milnacipran, citalopram, fluvoxamine, paroxetine, sertraline, escitalopram, and salts thereof.

2. A pharmaceutical composition comprising aripiprazole in combination with at least one serotonin reuptake inhibitor selected from the group consisting of fluoxetine, duloxetine, venlaflaxine, milnacipran, citalopram, fluvoxamine, paroxetine, sertraline and salts thereof.

3. A pharmaceutical composition comprising aripiprazole in combination with at least one serotonin reuptake inhibitor selected from escitalopram or a salt thereof.

4. The composition of claim 2, wherein the at least one serotonin reuptake inhibitor is citalopram.

5. The composition of any one of claims 1, 2, 3 and 4, wherein aripiprazole is anhydrous aripiprazole crystals B.

6. The composition of any one of claims 1, 2, 3 and 4, further comprising at least one pharmaceutically acceptable carrier.

7. The composition of any one of claims 1, 2, 3 and 4, wherein the composition is useful for the treatment of depression or major depressive disorder.

8. The composition of any one of claims 1, 2, 3 and 4, wherein the composition is useful for the treatment of major depressive disorder or dementia with depressive symptoms.

9. The composition of any one of claims 1, 2, 3, and 4, wherein the composition is useful for the treatment of major depressive disorder, endogenous depression, melancholia, depression in combination with psychotic episodes, bipolar disorder with depressive phase, refractory depression, dementia of the Alzheimer's type with depressive symptoms, Parkinson's disease with depressive symptom, senile dementia, mood disorder associated with cerebral blood vessels and mood disorder following head injury.

10. A pharmaceutical composition comprising at least one metabolite of aripiprazole selected from the group consisting of dehydroaripiprazole, DM-1451 and DM-1452 in combination with at least one serotonin reuptake inhibitor selected from the group consisting of fluoxetine, duloxetine, venlafaxine, milnacipran, citalopram, fluvoxamine, paroxetine, sertraline, escitalopram and salts thereof.

11. The composition of claim 10, wherein the at least one serotonin reuptake inhibitor is citalopram.

12. The composition of claim 10, wherein the at least one serotonin reuptake inhibitor is escitalopram.

13. The composition of any one of claims 10 to 12 further comprising at least one pharmaceutically acceptable carrier.

14. The composition of any one of claims 10 to 12 wherein the composition is useful for the treatment of depression or major depressive disorder.

15. The composition of any one of claims 10 to 12, wherein the composition is useful for the treatment of major depressive disorder or dementia with depressive symptoms.

16. The composition of any one of claims 10 to 12, wherein the composition is useful for the treatment of major depressive disorder, endogenous depression, melancholia, depression in combination with psychotic episodes, bipolar disorder with depressive phase, refractory depression, dementia of the Alzheimer's type with depressive symptoms, Parkinson's disease with depressive symptom, senile dementia, mood disorder associated with cerebral blood vessels and mood disorder following head injury.

17. A method of treating a mood disorder selected from the group consisting of depression of major depressive disorder, dementia with depressive symptoms, major depressive disorder, endogenous depression, melancholia, depression incombination with psychotic episodes, bipolar disorder with depressive phase, refractory depression, dementia of the Alzheimer's type with depressive symptoms, Parkinson's disease with depressive symptoms, senile dementia, mood disorders associated with cerebral blood vessels and mood disorders following head injury in a patient comprising: administering to the patient an effective amount of a pharmaceutical composition which comprise(s) (a) a compound selected from aripiprazole or metabolite of aripiprazole wherein the metabolite of aripiprazole is selected from the group consisting of dehydroaripiprazole, DM-1451 and in combination with (b) at least one serotonin reuptake inhibitor selected from the group consisting of fluoxetine, duloxetine, venlafaxine, milnacipran, citalopram, fluvoxamine, paroxetine, sertraline, escitalopram, and salts thereof.

18. A method of treating a mood disorder selected from the group consisting of depression of major depressive disorder, dementia with depressive symptoms, major depressive disorder, endogenous depression, melancholia, depression in combination with psychotic episodes, bipolar disorder with depressive phase, refractory depression, dementia of the Alzheimer's type with depressive symptoms, Parkinson's disease with depressive symptoms, senile dementia, mood disorders associated with cerebral blood vessels and mood disorders following head injury in a patient comprising: administering to the patient an effective amount of a pharmaceutical composition comprising aripiprazole in combination with at least one serotonin reuptake inhibitor selected from the group consisting of fluoxetine, duloxetine, venlafaxine, milnacipran, citalopram, fluvoxamine, paroxetine, sertraline and salts thereof.

19. A method of treating mood disorder selected from the group consisting of depression of major depressive disorder, dementia with depressive symptoms, major depressive disorder, endogenous depression, melancholia, depression in combination with psychotic episodes, bipolar disorder with depressive phase, refractory depression, dementia of the Alzheimer's type with depressive symptoms, Parkinson's disease with depressive symptoms, senile dementia, mood disorders associated with cerebral blood vessels and mood disorders following head injury in a patient comprising: administering to the patient of an effective amount of a pharmaceutical composition comprising aripiprazole in combination with at least one serotonin reuptake inhibitor selected from escitalopram and salt thereof.

20. The method of claim 18, wherein at least one serotonin reuptake inhibitor is citalopram.

21. The method of any one of claims 17 to 20, wherein aripiprazole is anhydrous aripiprazole crystals B.

22. The method of any one claims 17 to 20, wherein the pharmaceutical composition further comprises at least one pharmaceutically acceptable carrier.

23. The method of any one claims 17 to 20, wherein the mood disorder is useful for the treatment of depression of major depressive disorder.

24. The method of any one of claims 17 to 20, wherein the mood disorder is useful for the treatment of major depressive disorder or dementia with depressive symptoms.

25. The method of any one of claims 17 to 20, wherein the mood disorder is useful for the treatment of major depressive disorder, endogenous depression, melancholia, depression in combination with psychotic episodes, bipolar disorder with depressive phase, refractory depression, dementia of the Alzheimer's type with depressive symptoms, Parkinson's disease with depressive symptom, senile dementia, mood disorder associated with cerebral blood vessels or mood disorder following head injury.

26. A method of treating a mood disorder selected from the group consisting of depression of major depressive disorder, dementia with depressive symptoms, major depressive disorder, endogenous depression, melancholia, depression in combination with psychotic episodes, bipolar disorder with depressive phase, refractory depression, dementia of the Alzheimer's type with depressive symptoms, Parkinson's disease with depressive symptoms, senile dementia, mood disorders associated with cerebral blood vessels and mood disorders following head injury in a patient comprising: administering to the patient of an effective amount of pharmaceutical composition comprising at least one metabolite of aripiprazole selected from the group consisting of dehydroaripiprazole, DM-1451 and DM-1452 DM in combination with at least one serotonin reuptake inhibitor selected from the group consisting of fluoxetine, duloxetine, venlafaxine, milnacipran, citalopram, fluvoxamine, paroxetine, sertraline, escitalopram and salts thereof.

27. The method of claim 26, wherein the at least one serotonin reuptake inhibitor is citalopram.

28. The method of claim 26, wherein the at least one serotonin reuptake inhibitor is escitalopram.

29. The method of any one of claims 26 to 28, wherein the pharmaceutical composition further comprises at least one pharmaceutically acceptable carrier.

30. The method of any one of claims 26 to 28, wherein the mood disorder is useful for the treatment of depression of major depressive disorder.

31. The method of any one of claims 26 to 28, wherein the mood disorder is useful for the treatment of major depressive disorder or dementia with depressive symptoms.

32. The method of any one of claims 26 to 28, wherein the mood disorder is useful for the treatment of major depressive disorder, endogenous depression, melancholia, depression in combination with psychotic episodes, bipolar disorder with depressive phase, refractory depression, dementia of the Alzheimer's type with depressive symptoms, Parkinson's disease with depressive symptom, senile dementia, mood disorder associated with cerebral blood vessels or mood disorder following head injury.

* * * * *